(12) United States Patent
Liu et al.

(10) Patent No.: US 11,866,458 B2
(45) Date of Patent: Jan. 9, 2024

(54) PANAXADIOL GLYCOSIDE DERIVATIVE AND PREPARATION METHOD AND APPLICATION THEREOF

(71) Applicant: SUZHOU JI ER BIOLOGICAL MEDICINE CO., LTD., Suzhou (CN)

(72) Inventors: Quanhai Liu, Shanghai (CN); Jun Zhang, Shanghai (CN)

(73) Assignee: Suzhou JI ER Biological Medicine Co. Ltd., Jiangsu (CN)

( * ) Notice: Subject to any disclaimer, the term of this patent is extended or adjusted under 35 U.S.C. 154(b) by 0 days.

(21) Appl. No.: 16/764,090

(22) PCT Filed: Jul. 15, 2019

(86) PCT No.: PCT/CN2019/095992
§ 371 (c)(1),
(2) Date: May 14, 2020

(87) PCT Pub. No.: WO2019/219098
PCT Pub. Date: Nov. 21, 2019

(65) Prior Publication Data
US 2021/0054019 A1    Feb. 25, 2021

(30) Foreign Application Priority Data
May 15, 2018 (CN) .......................... 201810497184.5

(51) Int. Cl.
C07J 17/00 (2006.01)
A61P 11/06 (2006.01)

(52) U.S. Cl.
CPC ............. C07J 17/005 (2013.01); A61P 11/06 (2018.01)

(58) Field of Classification Search
CPC ...... C07J 17/005; C07J 41/0016; A61P 11/06; A61P 11/00; A61P 29/00
USPC ......................................................... 514/26
See application file for complete search history.

(56) References Cited

FOREIGN PATENT DOCUMENTS

| CN | 101781352 A | * | 7/2010 | ............... C07J 17/00 |
| CN | 102796159 A | | 11/2012 | |
| CN | 104586860 A | | 5/2015 | |
| CN | 109553653 A | | 4/2019 | |

OTHER PUBLICATIONS

Liao et al., Tetrahedron Letters, 2011, 52, 3075-3078.*
Ren et al., Bioorganic & Medicinal Chemistry Letters, Jan. 1, 2019, 29, 51-55.*
Deng, Xu et al. Exploring of drug leads from diversity-oriented Michael-acceptor library derived from natural products. Nat. Pro. Bioprospect., No. No. 2, Dec. 31, 2012 (Dec. 31, 2012).
Ren, Sumei et al. Synthesis and biological evaluation of Ginsenoside Compound K analogues as a novel class of anti- asthmatic agents. Bioorganic & Medicinal Chemistry Letters. vol. vol. 29,Nov. 9, 2018 (Nov. 9, 2018).
Atopkina, L. N. et al. Synthesis of 20S-protopanaxadiol 20-O-β-D-glucopyranoside, a metabolite of Panax ginseng glycosides, and compounds related to it. Chemistry of Natural Compounds, vol. 42, No.(4), Dec. 31, 2006 (Dec. 31, 2006).
Liao, Jinxi et al. Synthesis of ginsenoside Rh2 and chikusetsusaponin-LT8 via gold(I)-catalyzed glycosylation with a glycosyl ortho-alkynylbenzoate as donor. Tetrahedron Letters, vol. vol. 52, Apr. 7, 2011 (Apr. 7, 2011).

* cited by examiner

*Primary Examiner* — Ganapathy Krishnan
(74) *Attorney, Agent, or Firm* — Grogan, Tuccillo & Vanderleeden, LLP

(57) ABSTRACT

The invention discloses a panaxadiol glycoside derivative and a preparation method and application thereof. Such compounds show strong anti-inflammatory effects in vitro and in animal model experiments, and thus can be used to prepare anti-inflammatory drugs, especially can be used for treating asthma and COPD. In the experiment, the above-mentioned compounds have obvious effects on asthma and COPD, and the efficacy of the high-dose group is superior than that of dexamethasone and budesonide. Even under the dose much exceeding the therapeutic dose, no obvious affect on blood routine and blood glucoseis observed. It has high industrial prospects in the field of anti-inflammatory drugs, especially in the field for treating asthma and COPD.

13 Claims, 2 Drawing Sheets

PANAXADIOL GLYCOSIDE DERIVATIVE AND PREPARATION METHOD AND APPLICATION THEREOF

CROSS REFERENCE TO RELATED APPLICATIONS

This application is a National Stage of International Patent Application No. PCT/CN2019/095992 filed on Jul. 15, 2019, and claims priority to Chinese Patent Application No. 201810497184.5 filed on May 15, 2018, which are incorporated herein in their entireties.

TECHNICAL FIELD

The present invention relates to a ginsenoside derivative, in particular to a panaxadiol glycoside derivative, and also relates to a preparation method and application of the compound.

BACKGROUND

Asthma, also known as bronchial asthma, is a heterogeneous disease characterized by chronic airway inflammation in which eosinophils, mast cells, T lymphocytes, neutrophils, airway epithelial cells and many other cells and cell components, etc., are involved. This kind of chronic inflammation is related to airway hyperresponsiveness. The clinical manifestations mainly comprise recurrent wheezing, shortness of breath, chest distress and/or cough and asthma.

Asthma is a common respiratory disease, which is recognized as one of the top four major persistent diseases in the medical community. It can be life-threatening when it is serious, and is listed as one of the top ten causes of death. According to the survey, there are about 25 million people in China and 300 million people in the world suffer from asthma. The global death rate of asthma is about $\frac{1}{100000}$. There are about 250,000 people died of asthma every year in the world, and it is rising rapidly.

Not only Asthma is a serious threat to people's physical and mental health, weakens the labor force, reduces the quality of life, but also is difficult to be cured. Asthma is prone to relapse. According to the reports of WHO, the economic consumption associated with asthma is even higher than the total consumption of tuberculosis and AIDS.

As the pathogenesis of asthma is very complex, it has not been fully elucidated so far. At present, the recognized mechanisms can be summarized as follows: 1. The mechanism of tracheitis, in addition to the above-mentioned cells (such as eosinophils, mast cells, T lymphocytes, neutrophils, airway epithelial cells, etc.), the involved cells also include mediators such as prostaglandins, active neuropeptides as well as IL-4, IL-5, IL-12, IL-13 and interferon, granulocyte-monocyte colony stimulating factor, etc. 2. The mechanism of immunoreaction and allergy, such as the increase of total IgE and specific IgE in serum. 3. The mechanism of neuroreceptor regulation in airway, adrenergic nerve and cholinergic nerve are closely related to asthma. 4. The imbalance of Th1/Th2 cells. 5. The imbalance of second messenger cAMP/cGMP. 6. Other mechanisms related to pathogenesis of asthma, such as genetic inheritance and airway remodeling, etc.

According to the pathophysiology of asthma, many antiasthmatic drugs have been developed, which can be generally divided into anti-inflammatory antiasthmatic drugs, antiallergic antiasthmatic drugs and bronchodilator drugs, etc. More specifically, the categories of the antiasthmatic drugs can be divided as below:

1. Allergic mediator blockers, the mechanism of which is to selectively make the cell membrane of mast cells stable, to reduce the release of allergic mediators by its degranulation, to decrease the sensitivity to various non-specific stimulation and airway hyperresponsiveness, to reduce the attack of bronchospasm. The main drugs include sodium cromoglycate, ketotifen and nedocromil, etc. The safety of sodium cromoglycate is good, but the effect is not ideal; Ketotifen can prevent the attack of endogenous, exogenous and mixed asthma, and has a certain central inhibition and anticholinergic effect; Nedocromil is a strong antiasthmatic drug against allergic inflammation at present, which is used as an inhalant with fewer adverse reactions.

2. Bronchodilators, which are commonly used antiasthmatic drugs and play an important role in the art. These drugs can be divided into β2 receptor agonists, theophylline drugs and cholinergic receptor blockers. 2.1. β2 receptor agonists: they belong to bronchodilators. 32 receptor is distributed in different effector cells of airway and lung tissue. It should activate adenylate cyclase by activating G-protein, so as to increase cAMP level in the smooth muscle cells of bronchus, relax the smooth muscle of bronchus, increase the function of ciliary movement and mucus elimination, reduce exudation and airway edema, inhibit inflammatory cell mediators. According to the function thereof, the category can be divided into four categories: (1) work rapidly with long duration of action, such as formoterol inhalant; (2) work slowly with long duration of action, such as salmeterol; (3) work slowly with short duration of action, such as oral medicine terbutaline, salbutamol and formoterol; (4) work rapidly with short duration of action, such as inhaled terbutaline or salbutamol. 2.2 Theophylline drugs: they are derivative of methylxanthine, and commonly used bronchodilators, whose mechanism of relaxing the smooth muscle of respiratory tract is multi-step. Short acting theophylline is not recommended for patients who have taken sustained release theophylline for a long time. Compared with aminophylline, doxofylline has significant effect, low adverse reactions and good patient tolerance. Theophylline drugs have certain side effects, so it is necessary to monitor the blood concentration and adjust the dosage. 2.3 Anticholinergic drugs (M-cholinergic receptor blockers): there are three subtypes of M-cholinergic receptor in the respiratory tract. At present, most of the commonly used anticholinergic drugs are nonselective blockers of M-cholinergic receptor. Because M2 receptor is blocked, the inhibitory feedback regulation of M2 receptor is cancelled, in which the contraction response of airway is strengthened. Therefore, anticholinergic drugs for asthma are currently committed to M3 cholinergic receptor blockers, but no breakthrough has been made so far. At present, inhalants like ipratropium bromide, tiotropium bromide, etc. are commonly used. Ipratropium bromide has a good selectivity to M3 receptor, and tiotropium bromide is a long acting anticholinergic drug. There are also other M3 receptor blockers such as oxitropium and tiotropium. Since these drugs block the M-cholinergic receptor, thus inhibit guanosine reductase, and thereby reduce the concentration of cGMP in cells to relax the smooth muscle of bronchus, but taking effect slowly, they are often used as second-line drugs.

3. Immunotherapeutic agents and others: in recent years, due to the development of immunology, the immune process of immune mediator and antibody has been clearly described, so monoclonal antibody, receptor blocker and DNA vaccine, can play a role by regulating Th1/Th2 balance, antigen-specific IgG blocking the immune damage of antigen-specific IgE, and directly inhibiting the immune effector cells, mainly including IgE monoclonal antibody, TNF-α, IL-5, IL-4 and IL-13, etc. At present, most of them are in the further study of efficacy and safety. In addition, magnesium sulfate is also used for the treatment of acute severe asthma, because magnesium ion is a natural calcium antagonist.

4. Anti-inflammatory antiasthmatic drugs: 4.1 Leukotrienes, which can be used alone to control asthma as a long acting drug, and can also be used as alternative drug for mild asthma and in combination for moderate to severe asthma, but the effect is not as good as hormone representative drugs. Leukotrienes drugs include montelukast, zafirlukast and zileuton, etc. Antileukotrienes drugs can improve lung function, relieve asthma symptoms, and reduce hormone dosage. It is to be noted that this kind of medicine has certain side effects. 4.2 Glucocorticoid drugs: chronic airway inflammation is the main cause of asthma, and glucocorticoids are the most effective drugs to control airway inflammation at present. They have multifaceted mechanisms, and their anti-inflammatory effects involve the effects on vasculitis cells and inflammatory mediators: (1) Glucocorticoids can directly constrict blood vessels and inhibit vasodilation and fluid exudation. (2) Glucocorticoids can inhibit the aggregation of leukocytes in the inflammatory area and the migration and aggregation of inflammatory cells in the airway mucosa. (3) Glucocorticoids can decrease the release of bone marrow mononuclear cells, increase the release of neutrophils, and inhibit the release of toxic oxygen free radicals which can cause tissue damage from neutrophils and macrophages. (4) Glucocorticoids can inhibit the function of fibroblasts, and thus inhibit the production of collagen and aminopolysaccharide. (5) Glucocorticoids can inhibit the production of cytokines and mediators related to inflammation. For example, glucocorticoids can inhibit the production of prostaglandins (PG), leukotrienes (LTs), IL-1, IL-2, IL-3, IL-4, IL-5, IL-6, IL-8, TNF α, GM-csf, etc. (6) Glucocorticoids can decrease the concentration of complement components in plasma. (7) Glucocorticoids can inhibit the histamine release from basophils. (8) Glucocorticoids can reduce the generation of IgG. (9) Glucocorticoids can inhibit the generation of NOA and adhesion molecules. (10) Glucocorticoids can increase the reactivity and antiallergic effect of β2 receptor. Long term clinical studies have shown that the above-mentioned drugs can improve lung function, reduce airway responsiveness, reduce symptoms, reduce the frequency and degree of attack, and improve the quality of life.

Glucocorticoid drugs can be administered orally, inhaled or intravenously, etc. According to the severity and duration of asthma attack, different ways of administration and different drugs can be used. Generally, inhalation is the first choice. Because the inhalation dose is low, and inhalant directly effects on the respiratory tract, plays a local anti-inflammatory role, decreases the airway responsiveness, and reduces the frequency and degree of attack. Fluticasone propionate, budesonide and ciclesonide are commonly used. For patients with serious illness and difficult to control by inhalation treatment, systemic administration can be considered, but the systemic adverse reactions are strong and should be noted, so systemic administration should be minimized. Oral administration is better than injection. Prednisone, prednisolone and methylprednisolone can be used for oral administration, because they have little effect on corticosteroids, relatively short half-life, and can be treated every other day. Hydrocortisone can be used for severe cases. After the condition is under control, they can be gradually reduced and maintained by inhalants, because this kind of drugs may have side effects of corticosteroids, leading to spread of infection, aggravation of ulcer, gastrointestinal bleeding, hypertension, blood glucose elevation, water-sodium retention, blood potassium reduction and other adverse reactions.

Glucocorticoids play a wide and powerful role in lung and tracheal inflammation. However, glucocorticoids, in long-term treatment, can produce side effects such as diabetes, osteoporosis, etc., which cause many limitations in clinical application. In order to improve the treatment index of this kind of drugs, the principle of prodrug or soft drug is used for drug design by many researchers, and structural modifications can also be carried out around the steroid parent nucleus. For example, the ciclesonide mentioned above, after inhalation into the lung, is activated by esterolysis to produce active metabolites and play a local anti-inflammatory role. Because of its low bioavailability in vivo (less than 1%), ciclesonide causes fewer adverse reactions.

At present, one kind of drugs under research is the regulator of selective glucocorticoid receptor, which can separate its anti-inflammatory effects and side effects. This has become an important direction of innovative drugs research.

After entering the cytoplasm through the cell membrane, glucocorticoid binds with glucocorticoid receptor of specific inactive type in the cytoplasm, resulting in the change of receptor conformation. Heat shock protein (HSP90) dissociates to form a complex of hormone (Gc) and receptor (GR), which transfers to the nucleus. GR is activated, transforming from DNA non-binding type to DNA binding type, and then binds with specific DNA on target gene. This gene sequence is involved in GR activation, which is called glucocorticoid responsive elements (GRE). It plays roles in transcriptional inhibition or activation of downstream genes, thus inducing or inhibiting the synthesis of active proteins or cytokines, wherein, the transcriptional inhibition refers to the transcriptional regulation of ligand activated transcription factors, such as nuclear factor NF-κB and activator protein-1 (AP-1), which can inhibit pro-inflammatory transcription through protein-protein interactions, so as to produce anti-inflammatory effect. In addition, GC can induce the production of an anti-inflammatory polypeptide, lipocortin LC, which can inhibit phospholipase, so as to inhibit the production of arachidonic acid, and then inhibit prostaglandins (PGs) leukotrienes, platelet activating factor (PAF) and other inflammatory factors. GC can also induce an anti-inflammatory protein, which can inhibit the inflammatory response caused by histamine and 5-hydroxytryptamine. On the other hand, transcriptional activation refers to the binding of ligand activated GR in the form of dimer with glucocorticoid response element in the promoter/enhancer region of target gene to induce gene transcription, which is currently considered as the main mechanism of glucocorticoid side effects. Therefore, at present, many scientists in the medical field are studying the so-called selective glucocorticoid regulators, which can separate transcriptional activation and transcriptional inhibition. As drugs for chronic obstructive pulmonary disease (COPD), there have been reports of compounds entering clinical practice. Therefore, a large number of literatures on selective glucocorticoids show that scientists and pharmaceutical researchers all over the world attach great importance to this new method, and many well-known pharmaceutical companies have invested a lot of human and material resources in this aspect, hoping to make a breakthrough.

COPD is a common preventable and treatable disease characterized by persistent airflow obstruction. Airflow obstruction is usually progressive, which is related to the increase of chronic inflammatory response of airway and lung to toxic particles or gases. The occurrence of COPD and complications affect the overall severity of the disease. In the 2017 Global Initiative for chronic obstructive lung disease (Guide to GOLP), respiratory symptoms were raised to the same status as airway obstruction, highlighting the importance of symptoms in the prevention and treatment of this disease, in particular, it is emphasized that the abnormality of airway and lung tissue, the obstruction plays a certain role in the disease.

COPD is a common disease all over the world, which seriously affects the quality of life of patients and has high invalidism rate and mortality. At present, COPD is the fifth leading cause of death in the world, and is expected to become the third leading cause of death in the world after 2020. The increase of COPD incidence is closely related to tobacco use.

At the same time, COPD has a heavy economic burden on patients, families and society. According to the survey in some regions of China, the prevalence of COPD is as high as 8.2% in the 40 years old population. There are 400-600 million people suffering from COPD in the world.

Although there are some controversies, most scholars believe that pulmonary function is the gold index for diagnosis. The decrease of the ratio of forced expiratory volume in one second to forced expiratory volume (FFV0.2/FVC) indicates that the airflow is obstructed.

At present, it is believed that asthma and COPD overlap in symptoms and treatment methods, so it is called ACO (asthma-COPD overlap) in particular. These patients have low quality of life, rapid decline in lung function, frequent aggravation of the condition, and increased economic burden. In particular, the causal relationship between them is very clear. Some drugs in treatment are meaningful for both, so they have attracted various attentions.

Ginsenoside is a traditional Chinese medicine with a wide range of functions. Its chemical structure belongs to tetracyclic triterpenoids and is similar to glucocorticoids. One of the important pharmacology characteristics is its adaptogen effect, that is, its pharmacology often presents two-way effects due to different functional states of the body. For example, for pituitary-adrenal cortex system, it can not only prevent adrenal hypertrophy caused by Adrenocorticotropic hormone (ACTH), but also prevent adrenal atrophy caused by cortisone. Moreover, the effect of various ginsenosides on rat cortical hormone research results proves that ginsenoside Rd plays the strongest effect, that ginsenoside stimulates the adrenal cortex and increases the secretion of corticosteroids, and that it is not caused by adrenergic nervous system or excitation of H1 receptor. Therefore, it also showing that different ginsenosides have different effects on corticosteroids. In fact, in recent years, it has been proved that some ginsenosides have an agonistic effect on corticosteroid receptors, and some of the effects of ginsenosides are similar to modification agent of selective glucocorticoid.

The ginsenoside compound K (CK) is the main metabolite of original Panaxadiol type ginsenoside of ginseng in human intestine, which belongs to rare ginsenoside. The unique biological activity of ginsenoside CK has attracted extensive attention, and the scientific research on it is also increasing.

SUMMARY

According to the present invention, a series of compounds derived from panaxadiol glycoside have been studied, and found that such compounds exhibit high anti-inflammatory effects in vitro and in animal model experiments, and are particularly useful for treating asthma and COPD.

Specifically, the first aspect of the present invention relates to a panaxadiol glycoside derivative or a pharmaceutically acceptable salt thereof, the panaxadiol glycoside derivative is represented by the structure of the general formula (I) below:

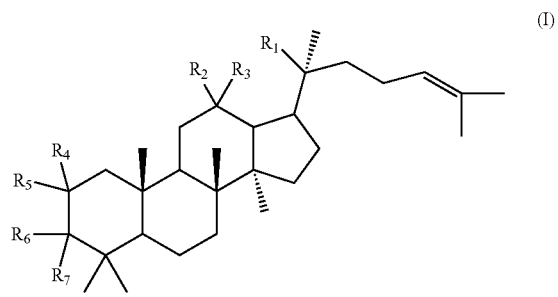

wherein, $R_1$ is selected from hydroxy or pyranosyl of non-glucose or

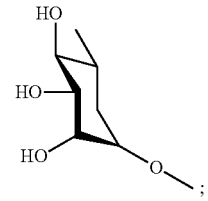

$R_2$ together with $R_3$ represents =O or =N—$OR_8$;

or $R_2$ is hydrogen and $R_3$ is hydroxyl;

$R_4$ and $R_6$ combine to form a bond, and $R_5$ and $R_7$ are independently selected from hydrogen, C1-6 alkoxy, hydroxyl, cyano group, C1-6 ester group, glycosyl;

or $R_6$ together with $R_7$ represents =O or =N—OH, and $R_5$ and $R_4$ are independently selected from hydrogen, C1-6 alkoxy, hydroxyl, cyano group;

or $R_4$, $R_5$, $R_6$ and $R_7$ are independently selected from hydrogen, C1-6 alkoxy, hydroxyl, cyano group, C1-6 ester group, glycosyl;

$R_8$ is selected from hydrogen or C1-6 alkyl.

According to one embodiment of the present invention, wherein $R_2$ together with $R_3$ represents =N—OH.

According to one embodiment of the present invention, wherein $R_4$ and $R_6$ combine to form a bond.

According to one embodiment of the present invention, wherein $R_6$ together with $R_7$ represents =N—$OR_8$; and $R_8$ represents hydrogen or methyl.

According to one embodiment of the present invention, wherein $R_4$ and $R_6$ combine to form a bond, $R_5$ is selected from glycosyl; and $R_1$ represents hydroxyl.

Wherein the C1-6 alkoxy refers to RO— group, wherein R refers to C1-6 alkyl, specifically including methoxy, ethoxy, propoxy, isopropoxy, butoxy, isobutoxy, tert-butoxy, pentoxy, isopentoxy, tert-pentyloxy, Neopentyloxy, hexyloxy, isohexyloxy, tert-hexyloxy, neohexyloxy, etc. The alkyl can be optionally substituted by the group selected from lower alkkyl, hydroxyl, cyano group.

The C1-6 alkoxy perferently is non-substituted methoxy or ethoxy.

The C1-6 ester group refers to RaCOO— group, wherein Ra refers to C1-5 alkyl; said C1-6 ester group perferently is acetoxyl group.

The pyranosyl glycosyl of non-glucose refers to rhamnopyranosyl, fucus glycosyl, arabinosyl glycosyl, xylosyl group, ribosyl group, quino-glycosyl, galactosyl, glucosamine group, 6-deoxy-6-glucosamine group, lactose group and cellobiose group.

The glycosyl refers to the part in the glycoside molecule that providing hemiacetal hydroxyl group, the glycosyl according to the present invention is preferably deoxy glycosyl and five carbon glycosyl, whose specific examples including ribulose group, rhamanopyranosyl, fucus glycosyl, arabinosyl glycosyl, xylosyl group, ribosyl group, quino-glycosyl, glucosyl group, galactosyl, glucosamine group, 6-deoxy-6-glucosamine group, lactose group and cellobiose group.

According to an embodiment of the present invention, wherein the present invention relates to the compounds below:

(IA)

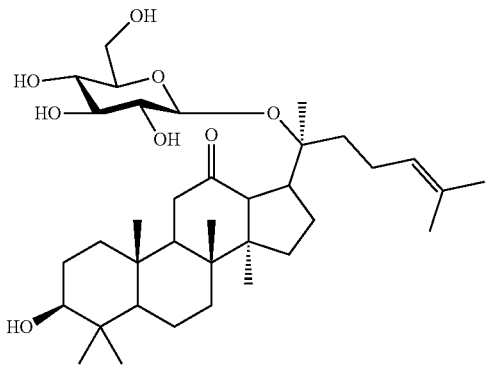

(IA-1)

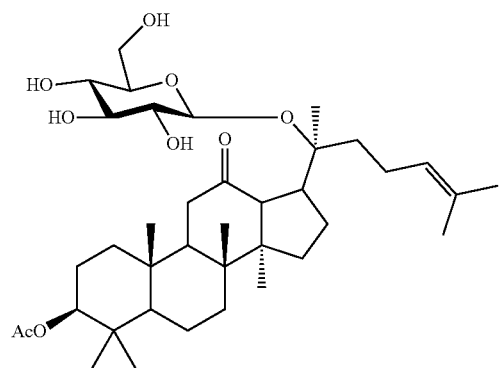

(IB)

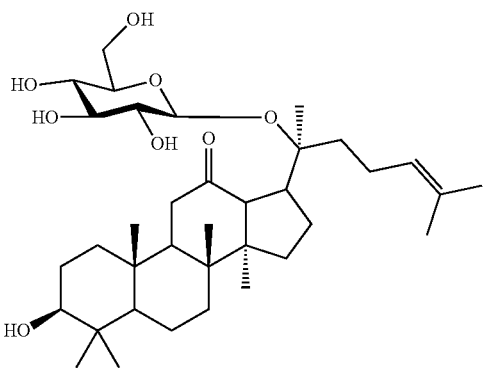

(IB-1)

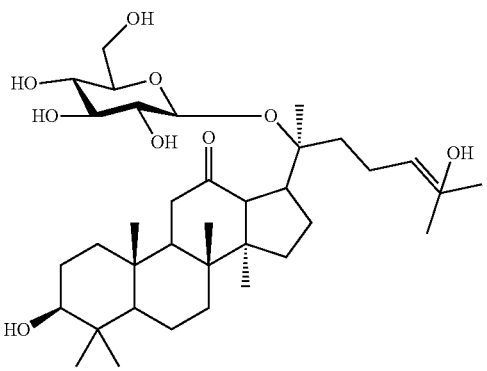

(IB-2)

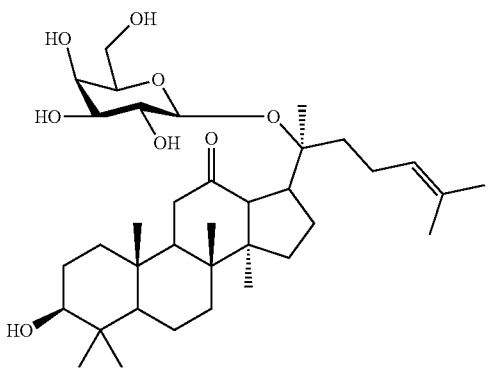

(IC)

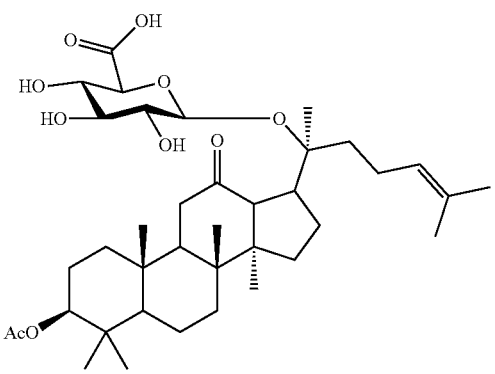

-continued
(ID)
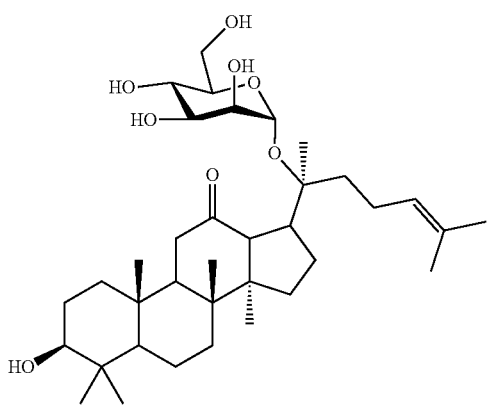
(IE)
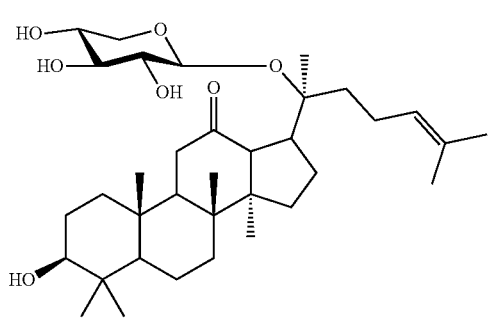
(IF)
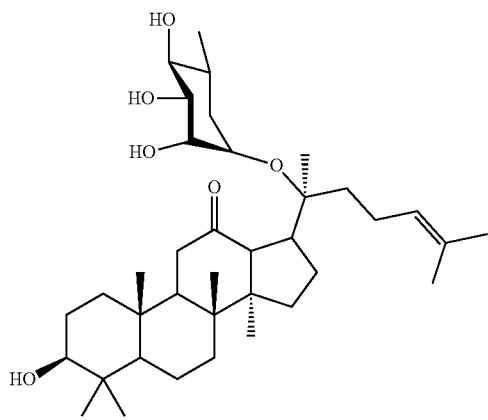
(IG)
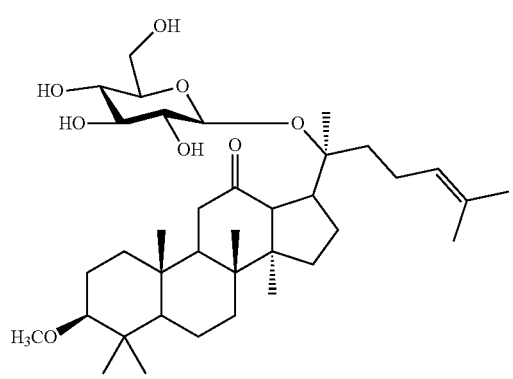
-continued
(IH)
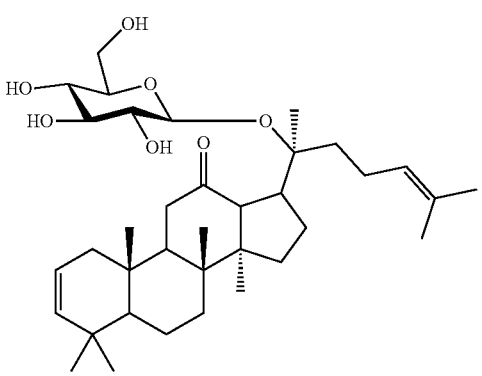
(IJ)
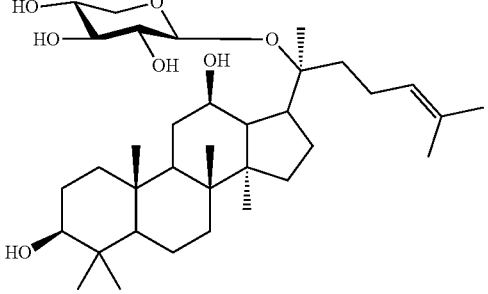
(IK)
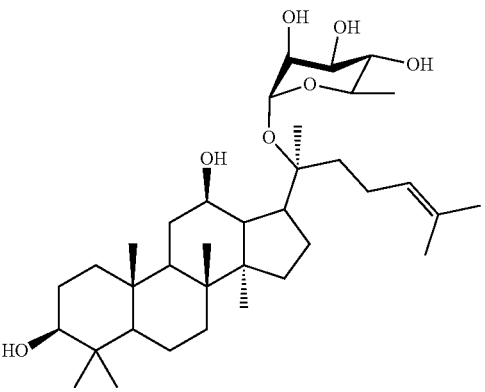
(IL)
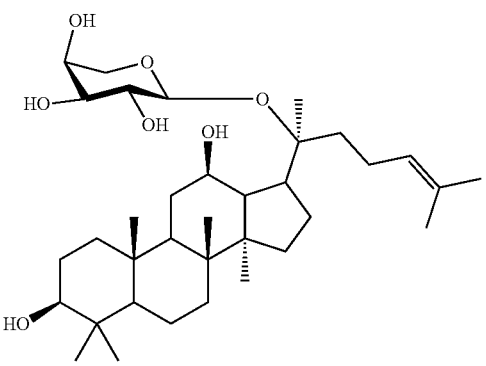

(IIA)
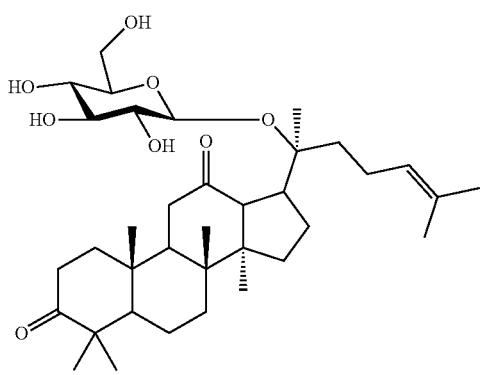

(IIA-1)
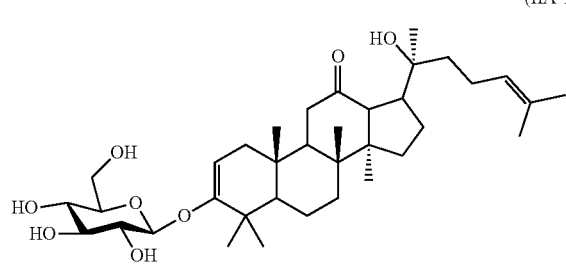

(IIB)
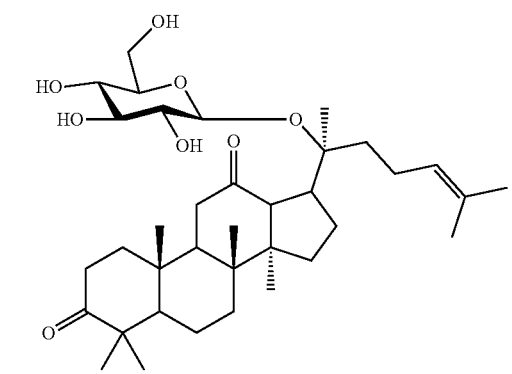

(IIIA)
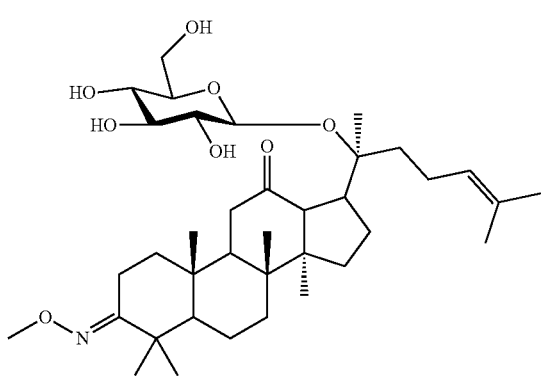

(IIIB)
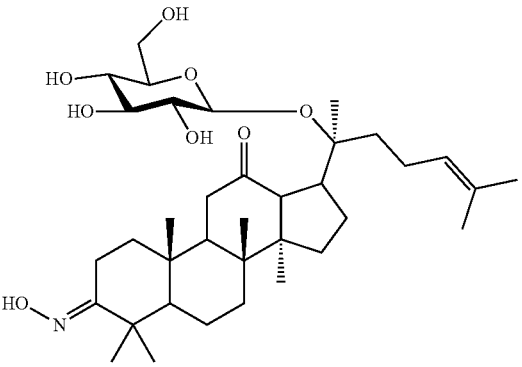

(IIIC)
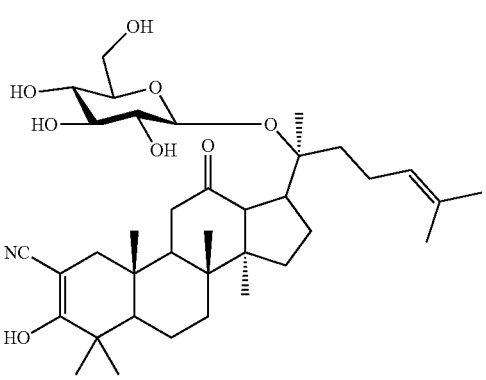

(IVA)
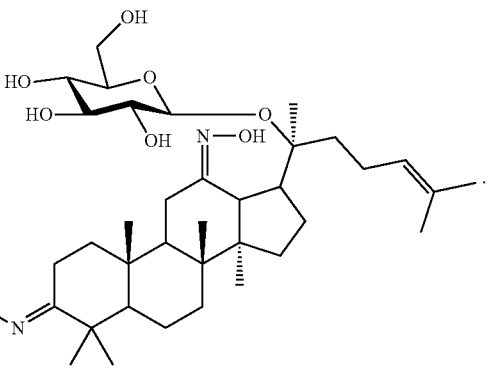

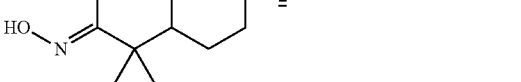

In the present invention the pharmaceutically acceptable salt is preferably an acid addition salt prepared by the reaction of a compound of the present invention with a pharmaceutically acceptable acid, or a salt prepared by the reaction of a compound with acidic group and a basic compound. Wherein the acid is preferably selected from inorganic acids (such as hydrochloric acid, sulfuric acid, phosphoric acid, or hydrogen bromic acid, etc.), and organic acids (such as oxalic acid, maleic acid, fumaric acid, malic acid, tartaric acid, citric acid, or Benzoic acid, etc.); the basic compound is preferably selected from sodium hydroxide, potassium hydroxide, calcium hydroxide, sodium carbonate, potassium hydrogen carbonate, ammonia or ammonium hydrogen carbonate. The above pharmaceutically acceptable salts are easily separated and can be purified by conventional separation methods, such as solvent extraction, dilution, recrystallization, column chromatography, and preparative thin-layer chromatography, etc. san diego lab.

Another aspect of the present invention relates to a synthetic method of the compounds of general formula (I), specifically relates to include reactions below:

1) Preparation of Selectively Diacyl Substituted 20 (S)-Panaxadiol Glycoside at 3 and 12 Positions The procedure of selectively acylation referring to: 20 (S)-panaxadiol glycoside (PPD) is to dissolve it in a organic solvent, after a catalyst is added, then 3 to 7 equivalents of the acylating agent is added, reaction by heating and obtained.

The acylating agent can be selected from one of acid anhydride, active ester or acyl chloride; acetic anhydride and benzoyl chloride are preferred.

catalyst is selected from one or a combination of dimethylaminopyridine, triethylamine, pyridine, diisopropylethylamine, or N, N, N, N-tetramethylethylenediamine. M Dimethylaminopyridine, and triethylamine are preferred.

2) Selective Deacylation of Acyl-Substituted 20 (S)-Panaxadiol Glycoside

Selective deacylation of 3,12-O-diacyl-substituted 20 (S)-panaxadiol glycoside in the presence of an organic base is performed to obtain the target compound.

The organic base is preferably a monovalent alkali metal compound; more preferably one or a combination of sodium methoxide, sodium ethoxide, sodium hydroxide, potassium hydroxide, and lithium hydroxide.

The reaction is preferably performed in the presence of an organic solvent, the organic solvent is selected from the group consisting of dichloromethane, chloroform, carbon tetrachloride, methanol, ethanol, propanol, butanol, acetonitrile, THF, DMF, DMSO, pyridine, benzene, toluene, xylene, ether, or mixtures thereof.

3) Glycoside Reaction

The substituted 20 (S)-panaxadiol glycoside is glycosylated in a glycoside treatment solution under the protection of an inert gas with a glycosyl donor, a Lewis acid catalyst and a molecular sieve, and a quencher is added to quench the reaction at the end of the reaction. Finally, it is purified by column chromatography or recrystallization to obtain a purified 20-O-glycosylation extract.

The molar ratio of the disubstituted 20 (S)-panaxadiol glycoside, the glycosyl donor and the Lewis acid catalyst is 1: (1.0-5.0): (0.01-0.5). The mass ratio of the disubstituted 20 (S)-panaxadiol glycoside and molecular sieve is 1:0.1-7:1.

The Lewis acid catalyst refers to one or a combination of C3-C9 haloamide, C1-C6 fluorohydrocarbon sulfonic acid, C2-C8 silicon fluorohydrocarbon sulfonate, C1-C6 silver fluorohydrocarbon sulfonate, boron trifluoride-diethyl ether complex or boron trifluoride-diethyl ether mixture.

The molecular sieve is a 3 Å-5 Å type aluminosilicate molecular sieve.

The glycoside treatment solution refers to one or a combination of C1-C4 chloroalkanes, toluene or ether.

The quencher is one or a combination of trimethylamine, triethylamine or sodium thiosulfate.

The eluent used in the column chromatography purification is one or a mixture of petroleum ether, dichloromethane, ethyl acetate, chloroform, methanol, n-hexane or cyclohexane.

The crystallization solvent used in the recrystallization purification is one or a combination of chloroform, C1-C4 alkyl alcohol, ethyl acetate, acetone, n-hexane, petroleum ether, cyclohexane, dichloromethane or water.

The organic solvent is one or a combination of methylene chloride, chloroform, pyridine, and dichloroethane.

4) Preparation of 20-O-Glycosyl Compound

The purified glycosylated extract can be produced under conditions similar to step 2) by selective deprotection reaction or complete deprotection reaction.

The polar solvent is one or a combination of tetrahydrofuran, methanol, ethanol, dichloromethane or water.

5) Oxidation of Hydroxyl Group

The hydroxyl groups at the 3 and 12 positions of the 20 (S)-panaxadiol glycoside derivative can be oxidized in the presence of an oxidant to obtain the corresponding oxo derivative.

The oxidant is one of dipyridium dichromate, pyridinium chromic anhydride, potassium dichromate, sodium dichromate, Dess-Martin oxidant, or chromium trioxide, or a mixture thereof.

The oxidation reaction is preferably carried out by heating in the presence of an organic solvent.

6) Reduction of Double Bond

The double bond in the 20 (S)-panaxadiol glycoside derivative can be reduced with hydrogen gas under the action of a hydrogenation catalyst to obtain the corresponding hydrogenated product.

The hydrogenation catalyst can be selected from Pd/C or other known hydrogenation catalyst.

The reaction is preferably performed in the presence of a polar solvent, said polar solvent is preferably methanol, ethanol.

7) Synthesis of 20 (S)-Hydroxydammarane-3, 24-Diene-12-One Compounds 20(S)-hydroxydammarane-3-hydroxyl-24-ene-12-one is reacted with acyl chloride under basic conditions, and then reacted with lithium bromide and lithium carbonate in DMF under heated to obtain the target compound.

The acyl chloride can be selected from benzenesulfonyl chloride, p-toluenesulfonyl chloride.

8) Preparation of 12-β-hydroxyl-20(S)-hydroxydammarane-24-ene-3-one Compounds

PPD is reacted with active acyl chloride in an organic solvent, in the presence of an organic base, at a low temperature, an acyl group is introduced at the 12-position of PPD. The acyl-substituted PPD is reacted at room temperature in the presence of PDC and acetic anhydride in an organic solvent, thereby the hydroxyl at the 3-position of the compound is oxidized into a carbonyl group. It is then stripped of the acyl group at position 12 in the presence of sodium alkoxide/alcohol, the target compound is obtained.

9) Synthesis of 20 (S)-Dammarane-3,12-Hydroxyimino-24-Ene Compounds

The 20 (S)-dammarane-3,12-dioxo-24-ene compound is reacted with hydroxylamine hydrochloride under basic conditions to obtain the corresponding hydroxyl imine compound.

Another aspect of the present invention relates to a pharmaceutical composition comprising the above-mentioned panaxadiol glycoside derivative of the present invention or a pharmaceutically acceptable salt thereof and a pharmaceutically acceptable excipient.

According to the purpose of treatment, the pharmaceutical composition can be made into various types of unit dosage forms, such as tablets, pills, powders, liquids, suspensions, emulsions, granules, capsules, suppositories and injections (solutions and suspensions), etc.

In order to shape the pharmaceutical composition in the form of a tablet, any excipient known and widely used in the art may be used, for example, carriers, such as lactose, sugar, sodium chloride, glucose, urea, starch, calcium carbonate, kaolin, crystalline cellulose and silicic acid, etc.; binders, such as water, ethanol, propanol, ordinary syrup, glucose solution, starch solution, gelatin solution, carboxymethyl cellulose, shellac, methyl cellulose and potassium phosphate, polyvinylpyrrolidone, etc.; disintegrants, such as dry starch, sodium alginate, agar powder and kelp powder, sodium hydrogen carbonate, calcium carbonate, fatty acid esters of polyethylene dehydrated sorbitol, sodium dodecyl sulfate, monoglyceric stearate, starch and lactose, etc.; disintegration inhibitors, such as sugar, glycerol tristearate, coconut oil and hydrogenated oil etc.; adsorption accelerators, such as quaternary amine bases and sodium dodecyl sulfate, etc.; wetting agents, such as glycerol, starch, etc.; adsorbents, such as starch, lactose, kaolin, bentonite and colloidal silicic acid, etc.; and lubricants, such as pure talc, stearates, boric acid powder and polyethylene glycol, etc. If necessary, common coating materials can also be used for tablets to form sugar-coated tablets, enteric-coated tablets, film-coated tablets (such as gelatin-coated tablets), double-layer film tablets, and multi-layer tablets.

In order to shape the pharmaceutical composition in the form of a pill, any excipient known and widely used in the art may be used, for example, carriers, such as lactose, starch, coconut oil, hardened vegetable oil, kaolin and talc, etc.; adhesive, such as arabic gum powder, tragacanth powder, gelatin and ethanol, etc.; disintegrants, such as agar and kelp powder, etc.

In order to shape the pharmaceutical composition in the form of suppositories, any excipient known and widely used in the art may be used, for example, polyethylene glycol, coconut oil, higher alcohols, higher alcohol esters, gelatin and semi-synthetic glycerides, etc.

In order to prepare a pharmaceutical composition in the form of an injection, the solution and the suspension can be sterilized, and an appropriate amount of sodium chloride, glucose or glycerol is preferably added to prepare an injection isotonic with blood. When preparing injections, any carrier commonly used in the art may also be used, for example, water, ethanol, propylene glycol, ethoxylated isostearyl alcohol, polyoxylated isostearyl alcohol and fatty acid esters of polyethylene dehydrated sorbitol, etc. In addition, commonly used solubilizers, buffers and analgesics, etc. can be added too.

The content of the compound represented by formula I and the pharmaceutically acceptable salt thereof in the pharmaceutical composition of the present invention is not particularly limited, and can be selected within a wide range, and may generally be 1-70% by mass, preferably 1-30% by mass.

In the present invention, the method of administering the pharmaceutical composition is not particularly limited. According to the patient's age, gender and other conditions and symptoms, a suitable formulation can be selected for administration. For example, tablets, pills, solutions, suspensions, emulsions, granules, and capsules are administered orally; injections can be administered alone or mixed with injection delivery solutions (such as glucose solution and amino acid solutions) for intravenous injection, and if necessary, it can simply be intramuscularly, intradermally, subcutaneously or intraperitoneally injected; and suppositories are administered to the rectum.

Another aspect of the present invention relates to the medical application of the above-mentioned compounds. Specifically, the compounds exhibit strong anti-inflammatory effects in vitro and in animal model experiments, thus can be used to prepare anti-inflammatory drugs, particularly can be used for treating asthma and COPD. Under the dose much exceeding the therapeutic index, there is no significant affect on blood and blood glucose, which is clearly superior to selective glucocorticoids. Therefore, it has high application prospects in anti-inflammatory drugs, especially in the field of the treatment of asthma and COPD.

DETAILED DESCRIPTION

Example 1 3-O-acetyl-20(S)—O-β-D-glucopyranosyl Dammarane-24-ene-12-one (IA)

1.1 Synthesis of 3,12-di-O-acetyl-20(S)-panaxadiol Glycoside (I-1a)

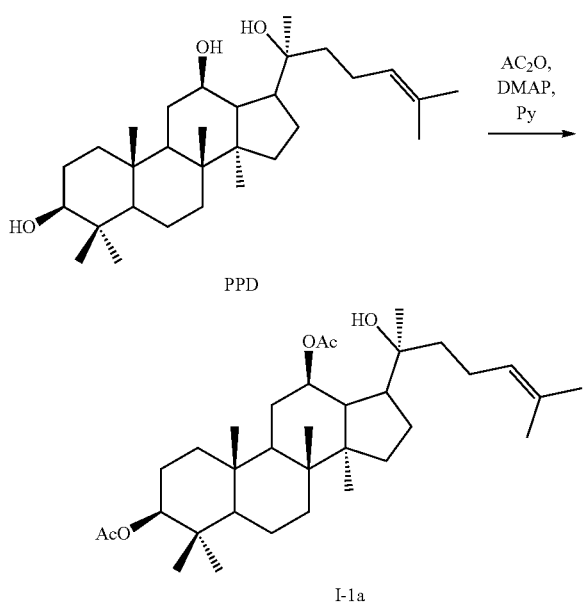

Figure 1:
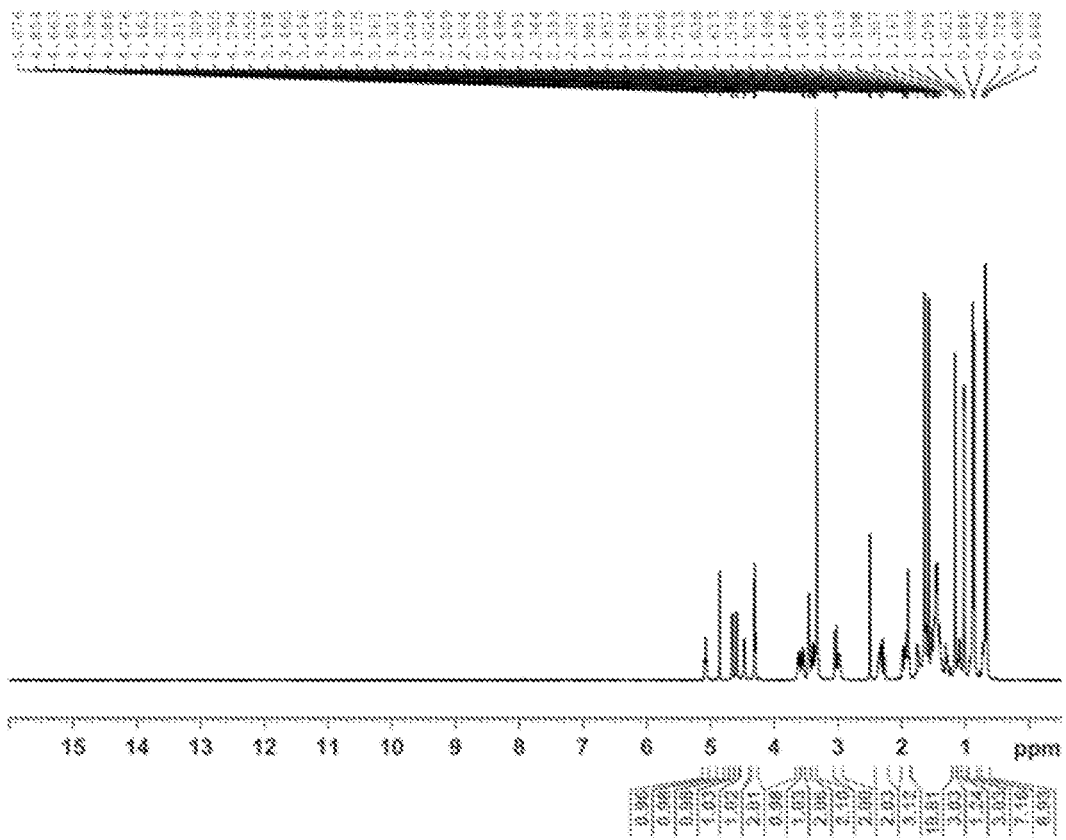
FIG. 1 is 1H NMR spectrum of compound IA-1.

20(S)-Panaxadiol glycoside (120.0 g, 0.26 mol) was dissolved in dry pyridine (750.0 mL), DMAP in a catalytic amount was added, Ac2O (99.1 mL, 1.04 mol) was dripped under ice bath, and the mixture was naturally restored to room temperature and reacted for 6.0 h. The reaction mixture was concentrated under reduced pressure, then diluted with ethyl acetate (2.0 L), washed successively with dilute hydrochloric acid, saturated NaHCO$_3$ aqueous solution and saturated NaCl aqueous solution. Organic layer was dried with anhydrous Na2SO4, after filtered and concentrated under reduced pressure, light yellow solid was obtained. After recrystallized (ethyl acetate/petroleum ether), white crystal I-1a (110.3 g, 77.8% yield) was obtained. 1H NMR (CDCl3) δ 5.15 (t, J=6.6 Hz, 1H, H-24), 4.72 (td, J=10.8, 4.8 Hz, 1H, H-12), 4.48 (dd, J=12.0, 4.2 Hz, 1H, H-3), 2.04 (s, 3H, H—COCH3), 2.03 (s, 3H, H—COCH3), 1.70 (s, 3H), 1.63 (s, 3H), 1.12 (s, 3H), 1.00 (s, 3H), 0.94 (s, 3H), 0.87 (s, 3H), 0.85 (s, 3H), 0.84 (s, 3H).

1.2 Synthesis of 3-β-O-acetyl-20(S)-panaxadiol glycoside (I-2a)

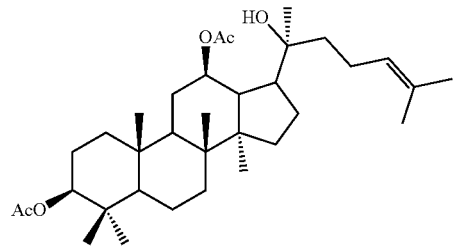

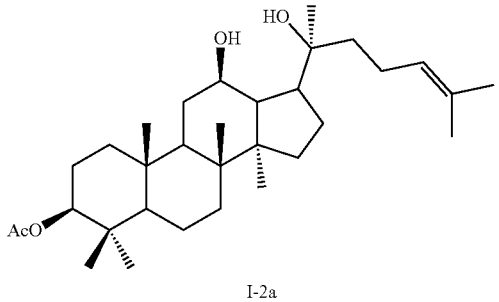

Compound I-1a (110.0 g, 0.20 mol) was dissolved in 100.0 mL of CH2Cl2, 400.0 mL methanol and MeONa (1.1 g, 0.02 mol) were added and reacted for 3.0 h at room temperature. Appropriate amount of cation resin was added to adjust pH to 7, and then the resin was removed through filtration. After concentration, light yellow solid I-2a (91.7 g, 90.3%) was obtained. 1H NMR (CDCl$_3$) δ 5.15 (t, J=6.6 Hz, 1H, H-24), 4.47 (dd, J=11.0, 5.5 Hz, 1H, H-3), 3.60 (td, J=10.5, 5.0 Hz, 1H, H-12), 2.04 (s, 3H, H—COCH3), 1.69 (s, 3H), 1.63 (s, 3H), 1.19 (s, 3H), 0.98 (s, 3H), 0.90 (s, 3H), 0.87 (s, 3H), 0.85 (s, 6H).

1.3 Synthesis of 3-β-O-acetyl-20(S)-hydroxyl dammarane-24-ene-12-one (I-3a)

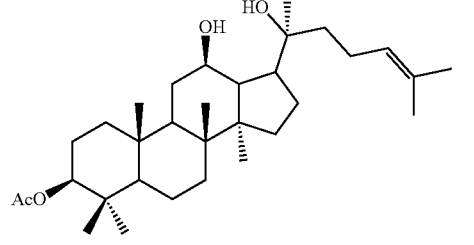

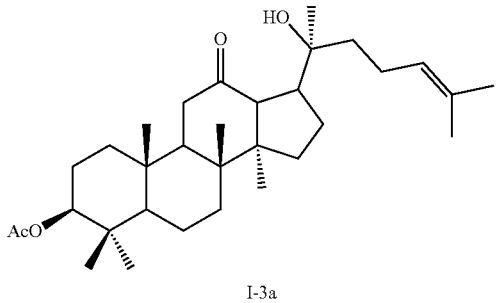

Compound I-2a (91.0 g, 0.18 mol) was dissolved in 500.0 mL of dried CH2Cl2, PDC (101.6 g, 0.27 mol) and acetic anhydride (34.0 mL, 0.36 mol) were added and reacted for about 5.0 h at room temperature. The insoluble substance was removed through suction filtration. The filtrate was concentrated and separated by column chromatography (ethyl acetate/n-hexane=1/10), and white crystal I-3a (63.4 g, 70.0%) was obtained. 1H NMR (CDCl3) δ 5.10 (s, 1H, H-24), 4.48 (dd, J=11.6, 4.4 Hz, 1H, H-3), 2.85 (d, J=10.2 Hz, 1H, H-13), 2.44-2.37 (m, 1H, H-17), 2.28 (d, J=14.3 Hz, 1H), 2.23 (d, J=14.0 Hz, 1H), 2.05 (s, 3H), 1.68 (s, 3H), 1.62 (s, 3H), 1.17 (s, 3H), 1.12 (s, 3H), 0.95 (s, 3H), 0.87 (s, 6H), 0.80 (s, 3H).

1.4 Synthesis of 3-β-O-acetyl-20(S)—O-β-D-glucopyranosyl dammarane-24-ene-12-one (IA)

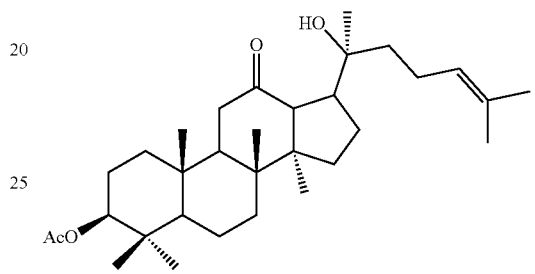

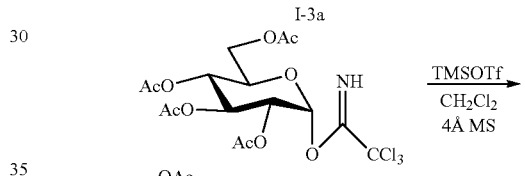

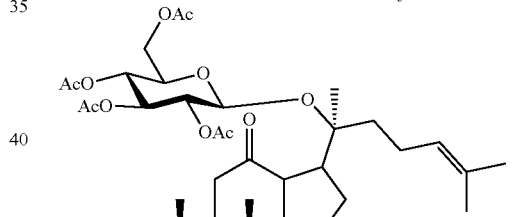

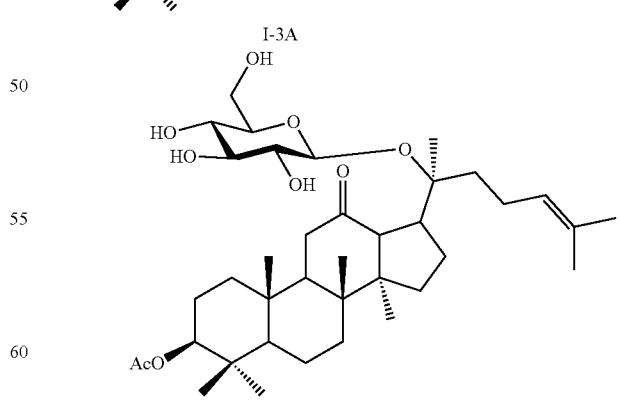

I-3a (25.0 g, 49.92 mmol) and 2,3,4,6-tetra-O-acetyl glucosamine trichloroimine ester (36.9 g, 74.88 mmol) were dissolved in dried CH2Cl2, appropriate amount of 4 Å molecular sieve was added, protected by argon, stirred for 30 min at room temperature, and then the temperature of the reaction system was reduced to −40° C., TMSOTf (901.69 μL, 4.99 mmol) was dripped, and reaction at −40° C. After TLC detection, Et3N was added to stop the reaction, restored to room temperature, the molecular sieve was removed by suction filtration, and the reaction solution was concentrated into solid. A quarter of the concentrate was dissolved in a mixed solvent of dichloromethane and methanol (400.0 mL, v:v=1:1), sodium methoxide was added to make pH=9-10, and then the mixture was reacted for 1.0 h at room temperature. The reaction was detected through TLC until it was completed. Cation resin was added to neutralize the reaction solution. After filtration, concentration and column chromatography, white solid IA (6.7 g, 81.0% two-step yield) was obtained. 1H NMR (400 MHz, CD3OD) δ 5.09 (t, J=6.5 Hz, 1H, H-24), 4.47-4.43 (m, 1H), 4.44 (d, J=7.6 Hz, 1H, H-1'), 3.80 (dd, J=11.7, 1.8 Hz, 1H), 3.64 (dd, J=11.8, 5.3 Hz, 1H), 3.36-3.32 (m, 2H), 3.27 (t, J=8.8 Hz, 1H), 3.22-3.18 (m, 1H), 3.10 (t, J=8.2 Hz, 1H), 2.51 (dd, J=9.7, 4.4 Hz, 1H), 2.44 (t, J=13.2 Hz, 1H), 2.11 (dd, J=12.8, 3.3 Hz, 1H), 2.02 (s, 3H), 1.66 (s, 3H), 1.62 (s, 3H), 1.27 (s, 3H), 1.11 (s, 3H), 1.02 (s, 3H), 0.91 (s, 3H), 0.88 (s, 3H), 0.76 (s, 3H); 13C NMR (150 MHz, CD3OD) δ 215.2, 172.8, 132.0, 126.0, 98.3, 82.5, 82.1, 78.8, 77.4, 75.7, 71.8, 62.9, 57.5, 57.2, 57.1, 56.1, 43.0, 41.9, 40.7, 40.7, 39.4, 39.0, 38.8, 35.5, 33.0, 28.5, 25.9, 25.0, 24.7, 24.6, 22.9, 21.2, 19.4, 17.8, 17.2, 16.9, 16.7, 16.3. MALDI-HRMS calcd for C38H62NaO9 [M+Na]+685.4286, found 685.4293.

Example 2 Preparation of 3-β-O-acetyl-20(S)—O-β-D-glucopyranuronic acid methyl ester dammarane-24-ene-12-one (IA-1)

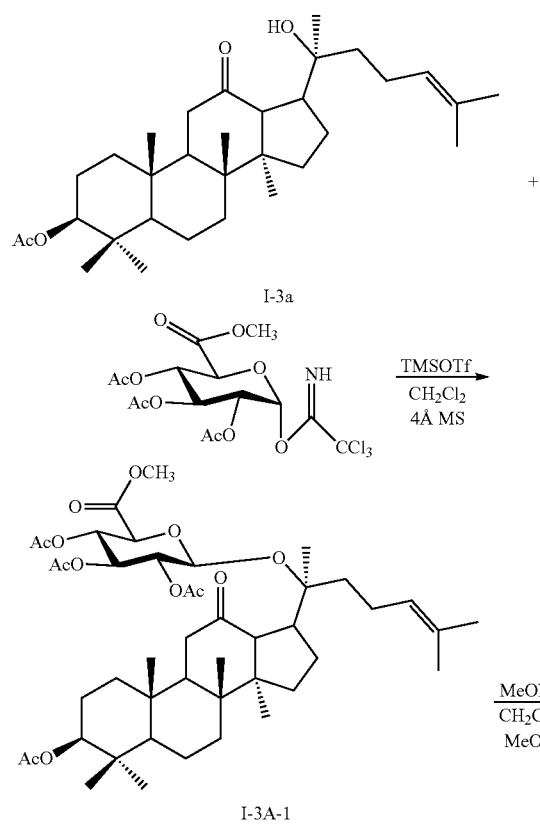

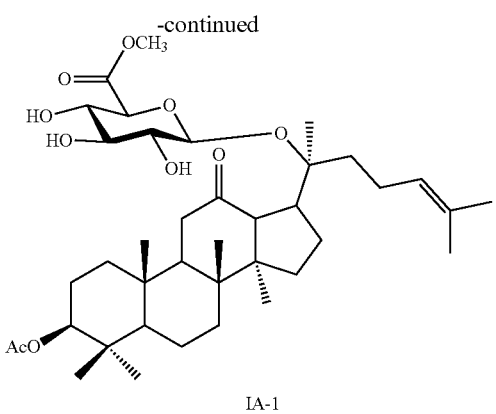

IA-1

I-3a (4.4 g, 8.79 mmol) and 2,3,4-tri-O-acetyl glucuronide methyl trichloroimine ester (5.0 g, 10.44 mmol) were dissolved in dried CH2Cl2, appropriate amount of 4 Å molecular sieve was added, protected by argon, stirred for 30 min at room temperature, then the temperature of the reaction system was reduced to −40° C., and TMSOTf (157.21 μL, 0.87 mmol) was dripped for reaction at −40° C. The reaction was detected through TLC until it was completed. Et3N was added to stop the reaction and is the mixture was restored to room temperature, the molecular sieve was removed through suction filtration, and the reaction solution was concentrated into solid. The concentrate was dissolved in a mixed solvent of dichloromethane and methanol (150.0 mL, v:v=1:1), sodium methoxide was added to make pH=9-10, then reaction was preformed for 1.0 h at room temperature. The reaction was detected through TLC until it was completed. Cation resin was added to neutralize the reaction solution, after filtration, concentration and column chromatography, white solid IA-1 (3.3 g, 54.1% two-step yield) was obtained. The 1H NMR (400 MHz, DMSO-D6) is shown in FIG. 1. 13C NMR (150 MHz, CD3OD) δ 215.1, 172.8, 171.3, 132.0, 125.9, 98.7, 83.0, 82.1, 77.9, 76.4, 75.2, 73.1, 57.4, 57.2, 57.1, 56.1, 52.8, 43.2, 41.9, 40.7, 40.4, 39.4, 38.9, 38.8, 35.4, 33.0, 28.4, 25.9, 25.0, 24.5, 24.4, 22.7, 21.1, 19.4, 17.8, 17.1, 16.9, 16.7, 16.3.

Example 3β-hydroxyl-20(S)—O-β-D-glucopyranosyl dammarane-24-ene-12-one (IB)

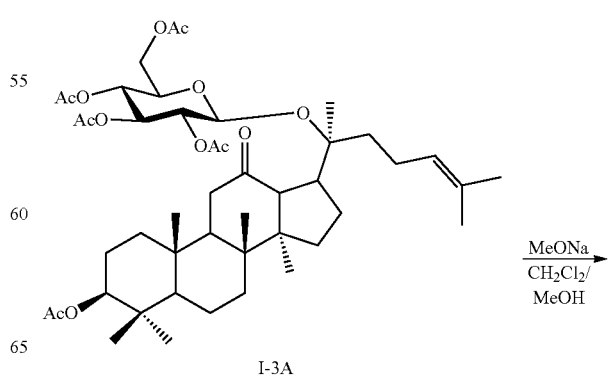

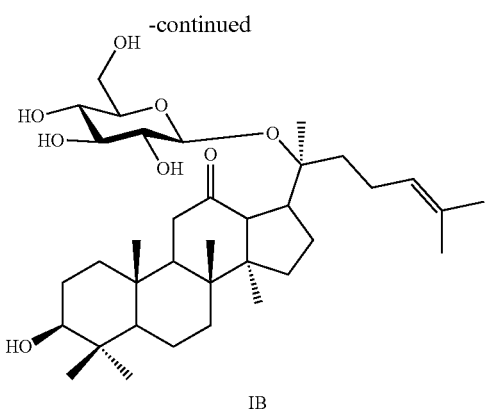

IB

Two quarters of the concentrate in step 1.4 of the example was dissolved in the mixed solvent of dichloromethane and methanol (400.0 mL, v:v=1:1), sodium methoxide was added to make pH=9-10. The reaction was allowed to take place for 6.0 h at 50° C. and detected through TLC until it was completed. Cation resin was added to neutralize the reaction solution, after filtration, concentration and column chromatography, white solid IB (11.6 g, 74.8% two-step yield) was obtained. 1H NMR (400 MHz, CD3OD) δ 5.09 (t, J=6.2 Hz, 1H), 4.44 (d, J=7.6 Hz, 1H, H-1'), 3.80 (d, J=11.5 Hz, 1H), 3.64 (dd, J=11.7, 5.3 Hz, 1H), 3.34-3.31 (m, 2H), 3.28 (t, J=8.8 Hz, 1H), 3.21-3.18 (m, 1H), 3.16-3.08 (m, 2H), 2.52-2.40 (m, 2H), 1.67 (s, 3H), 1.62 (s, 4H), 1.27 (s, 3H), 1.11 (s, 3H), 0.98 (s, 3H), 0.97 (s, 3H), 0.79 (s, 4H), 0.74 (s, 3H).

Example 4 3β-hydroxyl-20(S)—O-β-D-glucopyranosyl dammarane-12-one (IB-1)

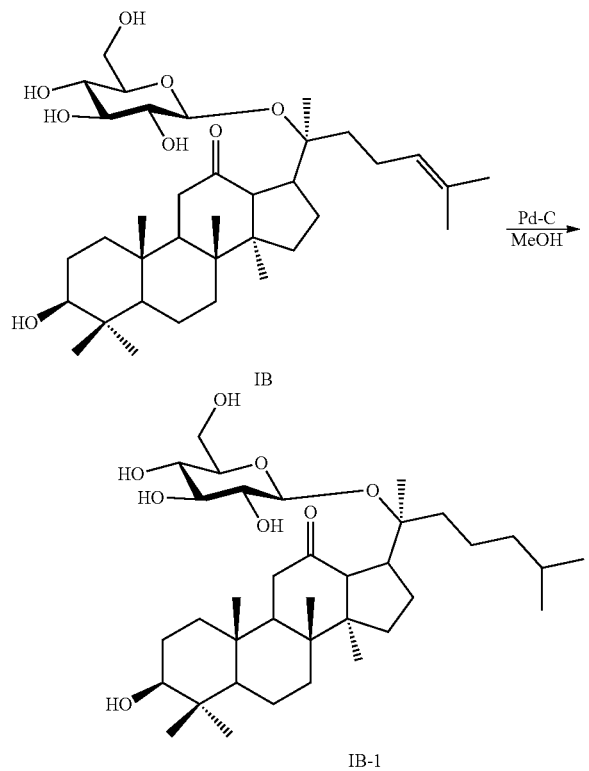

IB (7.5 g, 12.08 mmol) was dissolved in MeOH (200.0 mL), and then Pd/C (750.0 mg) was added. After H2 replacement, the reaction was allowed to take place for 2 h at room temperature and then detected through TLC until it was completed. Pd/C was removed through diatomite filtration, and after concentration and column chromatography (CH2Cl2/MeOH=10/1), white solid IB-1 (4.6 g, 61.3%) was obtained. 1H NMR (400 MHz, CD3OD) δ 4.43 (d, J=7.7 Hz, 1H), 3.80 (dd, J=11.6, 1.5 Hz, 1H), 3.64 (dd, J=11.6, 5.4 Hz, 1H), 3.36-3.31 (m, 2H), 3.27 (d, J=8.8 Hz, 1H), 3.21-3.17 (m, 1H), 3.15 (t, J=6.4, 4.8 Hz, 1H), 3.09 (t, J=8.4 Hz, 1H), 2.50-2.40 (m, 2H), 2.11 (dd, J=12.7, 3.5 Hz, 1H), 1.9-1.91 (m, 1H), 1.84-1.78 (m, 1H), 1.27 (s, 3H), 1.08 (s, 3H), 0.98 (s, 3H), 0.97 (s, 3H), 0.89 (s, 3H), 0.88 (s, 3H), 0.79 (s, 3H), 0.74 (s, 3H); 13C NMR (150 MHz, CD3OD) δ 215.6, 98.3, 82.6, 79.3, 78.8, 77.4, 75.6, 71.8, 62.9, 57.5, 57.2, 57.1, 56.3, 42.9, 41.9, 41.0, 40.7, 40.0, 40.0, 38.8, 35.6, 33.0, 29.0, 28.6, 27.9, 24.9, 23.8, 23.0, 22.9, 19.5, 17.1, 16.7, 16.3, 16.0. MALDI-HRMS calcd for C36H62NaO8 [M+Na]+ 645.4337, found 645.4354.

Example 5 3β, 25-dihydroxyl-20(S)—O-β-D-glucopyranosyl dammarane-12-one (IB-2)

5.1 Synthesis of 24-Br-25-hydroxyl-3β-O-acetyl-20(S)—O-(2,3,4,6-tetra-O-acetyl-β-D-glucopyranosyl) dammarane-12-one (I-3A-2)

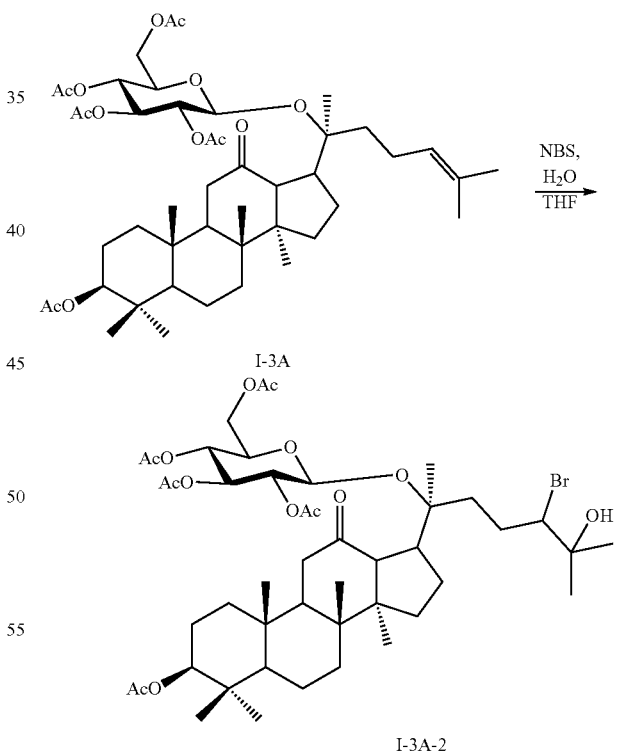

I-3A (7.5 g, 9.02 mmol) was dissolved in 150 mL of tetrahydrofuran, 15 mL of water was added, N-bromosuccinimide (2.4 g, 13.53 mmol) was added in batches under ice bath, and the reaction was continued for 1 h under ice bath. After the reaction was detected through TLC until it was completed, 200 mL of ethyl acetate was added to dilute the reaction solution, then washed with 5% sodium thiosulfate solution and saturated salt water in turn. The organic layer was dried with anhydrous sodium sulfate, and after filtration, concentration and column chromatography (ethyl acetate/petroleum ether=½), white solid I-3A-2 (7.6 g, 90.5%) was obtained. 1H NMR (400 MHz, CDCl3) δ 5.20 (t, J=9.4 Hz, 1H, H-3'), 5.01 (t, J=9.8 Hz, 1H, H-4'), 4.95 (t-like, J=9.0, 8.2 Hz, 1H, H-2'), 4.68 (d, J=7.8 Hz, 1H, H-1'), 4.46 (dd, J=11.4, 4.7 Hz, 1H, H-3), 4.12-4.18 (m, 2H, H-6'), 3.89 (d, J=9.8 Hz, 1H, H-24), 3.70-3.68 (m, 1H, H-5'), 2.97 (d, J=9.8 Hz, 1H, H-13), 2.38-2.44 (m, 1H, H-17), 2.16 (d, J=8.6 Hz, 2H, H-11), 2.10 (s, 3H, H—Ac), 2.04 (s, 3H, H—Ac), 2.02 (s, 3H, H—Ac), 1.98 (s, 6H, H—Ac*2), 1.35 (s, 3H, H-26, H-27), 1.19 (s, 3H, H-20), 1.04 (s, 3H, H-Me), 0.95 (s, 3H, H-Me), 0.87 (s, 3H, H-Me), 0.85 (s, 3H, H-Me), 0.72 (s, 3H, H-Me); 13C NMR (125 MHz, CDCl3) δ 211.3 (C-12), 170.9, 170.7, 170.2, 169.5, 169.1, 94.7 (C-1'), 81.8, 80.3, 73.1, 72.6, 72.1, 71.8, 71.7, 68.6, 62.4, 56.2, 55.8, 55.7, 54.3, 41.4, 40.5, 39.7, 38.6, 38.2, 37.8, 37.5, 34.2, 31.6, 29.1, 27.9, 26.5, 26.2, 23.7, 23.4, 22.8, 21.3, 20.8, 20.6, 18.2, 16.7, 16.4, 16.2, 15.6. MALDI-HRMS calcd for C46H71O14BrNa [M+Na]+949.3919, found 949.3919.

5.2 Synthesis of 25-hydroxyl-3β-O-acetyl-20(S)—O-(2,3,4,6-tetra-O-acetyl-β-D-glucopyranosyl) dammarane-12-one (I-3A-3)

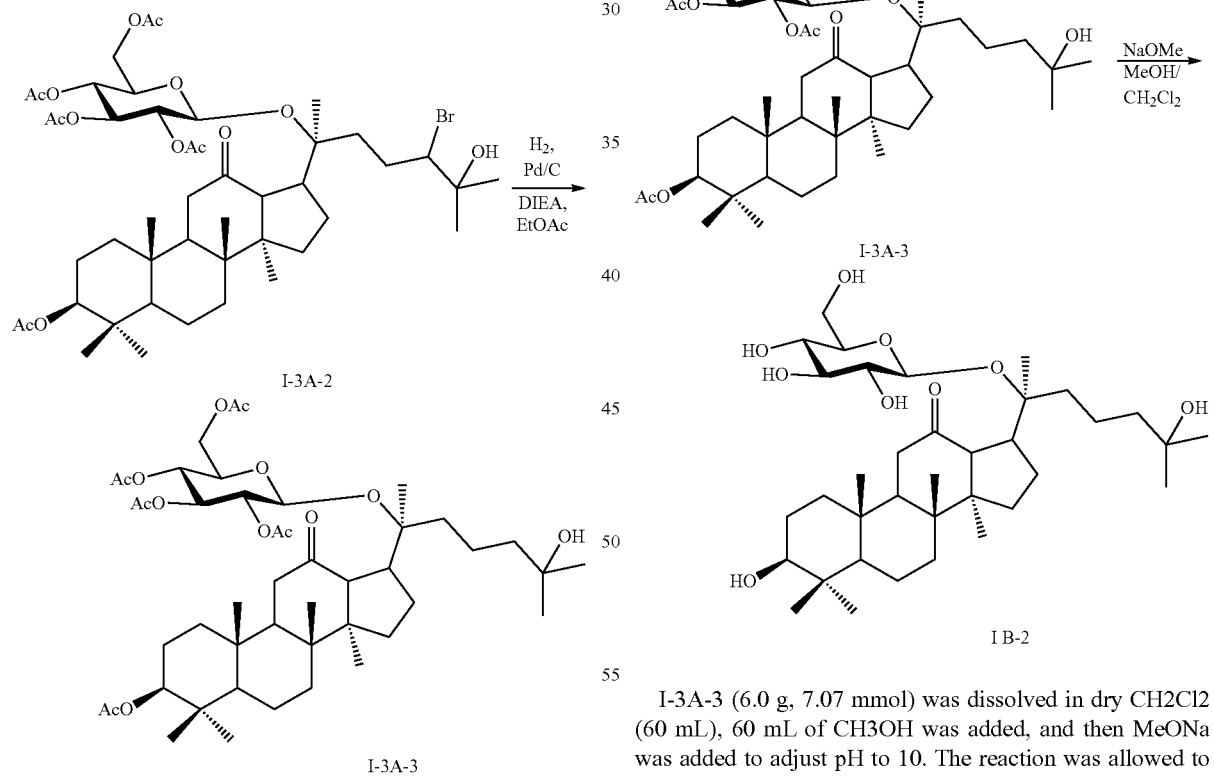

I-3A-2 (7.2 g, 7.76 mmol) was dissolved in 150 mL of EtOAc, DIEA 3 mL and Pd/C 720.0 mg was added, and after H2 replacement, the reaction was allowed to take place for 2 h at room temperature. The reaction was detected through TLC until it was completed. Pd/C was removed by diatomite filtration, the reaction solution was concentrated, and white solid I-3A-3 (6.0 g, 90.9%) was obtained by column chromatography (ethyl acetate/petroleum ether=1/1). 1H NMR (400 MHz, CDCl3) δ 5.17 (t, J=9.4 Hz, 1H, H-3'), 5.00 (t-like, J=9.9, 9.3 Hz, 1H, H-4'), 4.93 (t, J=8.8 Hz, 1H, H-2'), 4.61 (d, J=7.7 Hz, 1H, H-1'), 4.46 (dd, J=11.5, 4.4 Hz, 1H, H-3), 4.16 (dd, J=12.1, 6.1 Hz, 1H, H-6'-1), 4.09 (dd, J=12.1, 2.0 Hz, 1H, H-6'-2), 3.64 (ddd, J=9.9, 6.1, 2.2 Hz, 1H, H-5'), 2.98 (d, J=9.9 Hz, 1H, H-13), 2.45 (td, J=10.4, 5.5 Hz, 1H, H-17), 2.07 (s, 3H, H—Ac), 2.03 (s, 3H, H—Ac), 2.01 (s, 3H, H—Ac), 1.98 (s, 6H, H—Ac, H—Ac), 1.21 (s, 6H, H-26, H-27), 1.19 (s, 3H, H-21), 1.02 (s, 3H, H-Me), 0.95 (s, 3H, H-Me), 0.87 (s, 3H, H-Me), 0.85 (s, 3H, H-Me), 0.72 (s, 3H, H-Me); 13C NMR (125 MHz, CDCl3) δ 211.6 (C-12), 170.8 (C—Ac), 170.6 (C—Ac), 170.2 (C—Ac), 169.5 (C—Ac), 169.0 (C—Ac), 94.6 (C-1'), 82.3, 80.4, 73.2, 71.9, 71.5, 70.7, 68.8, 62.6, 56.1, 55.8, 55.6, 54.5, 44.7, 41.2, 40.5, 39.7, 39.6, 38.3, 37.9, 37.5, 34.3, 29.4, 29.3, 27.9, 23.5, 23.5, 23.2, 21.2, 20.8, 20.6, 19.6, 18, 2, 16.8, 16.4, 16.2, 15.6. MALDI-HRMS calcd for C46H72O14Na [M+Na]+ 871.4820, found 871.4824.

5.3 Synthesis of 3 (3β, 25-dihydroxyl-20(S)—O-β-D-glucopyranosyl dammarane-12-one (IB-2)

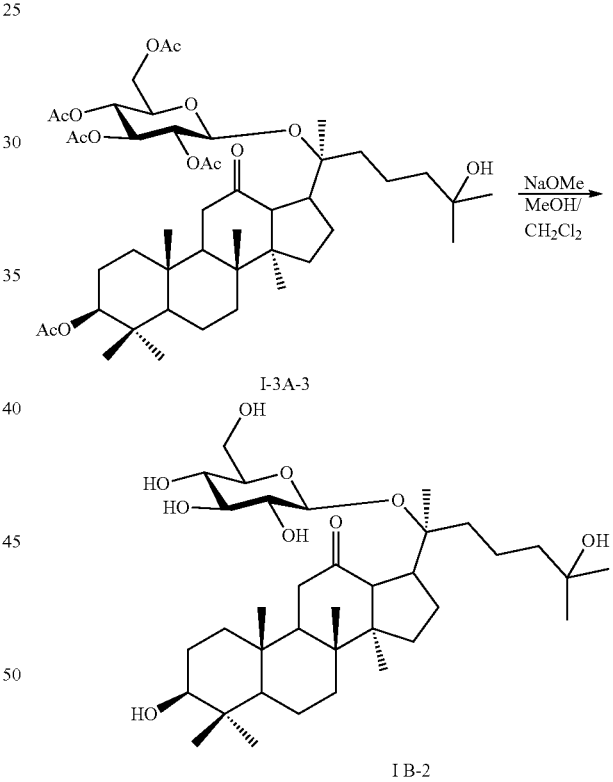

I-3A-3 (6.0 g, 7.07 mmol) was dissolved in dry CH2Cl2 (60 mL), 60 mL of CH3OH was added, and then MeONa was added to adjust pH to 10. The reaction was allowed to take place for about 6 h at 48° C. Appropriate amount of cation resin was added to adjust pH to neutral, then the resin was removed through filtering, and after concentrating and column chromatography (CHCl3/CH3OH=15/1), white solid IB-2 (3.9 g, 86.6%) was obtained. 1H NMR (400 MHz, CD3OD) δ 4.44 (d, J=7.7 Hz, 1H), 3.81 (dd, J=11.8, 1.8 Hz, 1H), 3.63 (dd, J=11.8, 5.5 Hz, 1H), 3.34-3.31 (m, 2H), 3.27 (t, J=9.0 Hz, 1H), 3.23-3.18 (m, 1H), 3.15 (t, J=6.0, 4.8 Hz, 1H), 3.09 (t, J=8.4 Hz, 1H), 2.50 (dd, J=9.5, 4.3 Hz, 1H), 2.43 (t, J=13.2 Hz, 1H), 2.11 (dd, J=12.7, 3.3 Hz, 1H), 1.95-1.90 (m, 1H), 1.27 (s, 3H), 1.17 (s, 6H), 1.11 (s, 3H), 0.98 (s, 3H), 0.97 (s, 3H), 0.79 (s, 3H), 0.75 (s, 3H); 13C NMR (150 MHz, CD3OD) δ 215.6, 98.3, 82.7, 79.3, 78.7, 77.5, 75.6, 71.8, 71.5, 62.9, 57.5, 57.2, 57.2, 56.3, 45.5, 43.3, 41.9, 41.3, 40.7, 40.0, 39.9, 38.8, 35.6, 33.0, 29.4, 29.2, 28.6, 27.9, 25.0, 22.9, 20.6, 19.5, 17.1, 16.7, 16.3, 16.0. MALDI-HRMS calcd for C36H62O9Na [M+Na]+661.4292, found 661.4304.

According to the same methods above, other panaxadiol glycoside derivatives having different glycosyl groups were prepared.

Example 6 3p-hydroxyl-20(S)—O-β-D-galactopyranosyl dammarane-24-ene-12-one(IC)

White solid, 5.2 g, two-step yield is 70.3%. 1H NMR (400 MHz, CD3OD) δ 5.08 (t, J=6.8 Hz, 1H, H-24), 4.39 (d, J=6.2 Hz, 1H, H-1'), 3.82 (s, 1H), 3.71 (dd, J=10.6, 6.6 Hz, 1H), 3.64 (dd, J=10.8, 6.4 Hz, 1H), 3.46-3.42 (m, 3H), 3.35 (d, J=9.4 Hz, 1H), 3.14 (dd, J=10.7, 4.5 Hz, 1H), 2.52-2.40 (m, 2H), 2.11 (dd, J=12.7, 2.3 Hz, 1H), 1.66 (s, 4H), 1.62 (s, 3H), 1.27 (s, 3H), 1.11 (s, 3H), 0.98 (s, 3H), 0.97 (s, 3H), 0.80 (s, 3H), 0.74 (s, 3H); 13C NMR (150 MHz, CD3OD) δ 215.6, 131.9, 126.0, 98.8, 82.4, 79.3, 76.1, 75.6, 73.1, 70.1, 62.1, 57.5, 57.2, 57.1, 56.4, 43.0, 41.9, 40.7, 40.6, 40.0, 39.9, 38.8, 35.6, 33.0, 28.6, 27.9, 25.9, 24.9, 24.7, 22.9, 19.5, 17.8, 17.1, 16.7, 16.3, 16.0.

MALDI-HRMS calcd for C36H60NaO8 [M+Na]+ 643.4180, found 643.4190.

Example 7 3β-hydroxyl-20(S)—O-α-D-mannopyranosyl dammarane-24-ene-12-one (ID)

Figure 2:
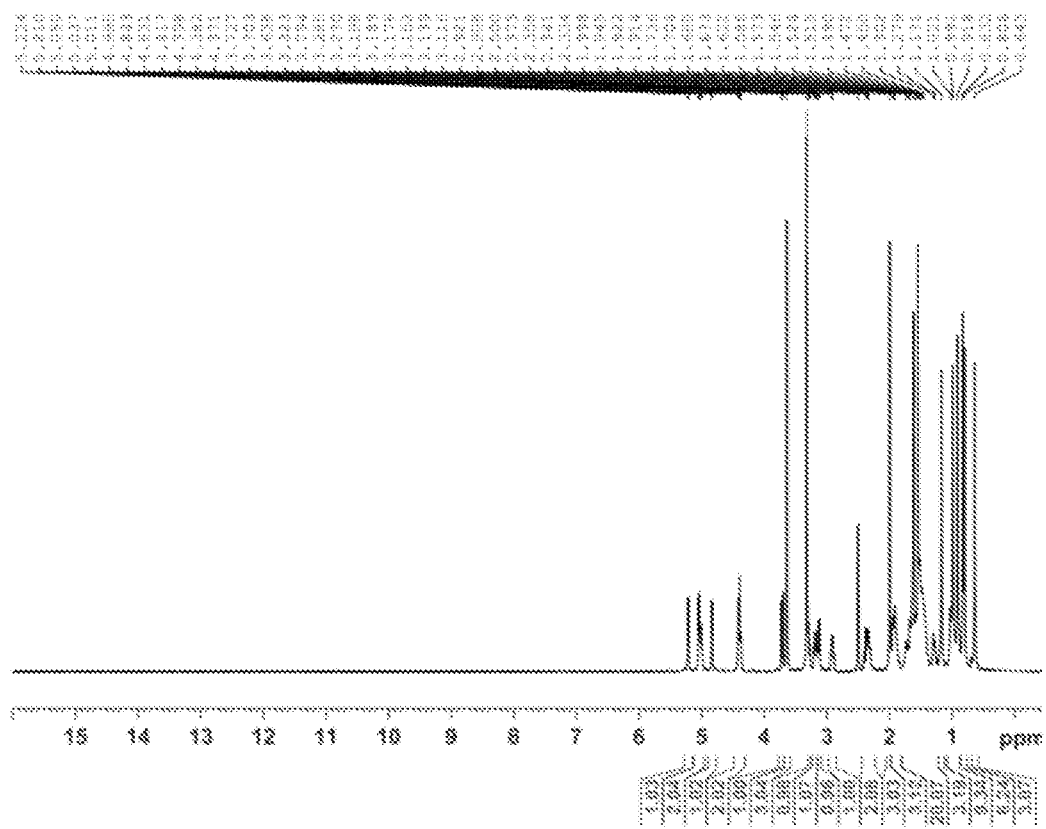
FIG. 2 is 1H NMR spectrum of compound ID.

White solid, 4.9 g, two-step yield is 66.2%, whose 1H NMR ((400 MHz, DMSO-D6)) is showed in FIG. 2; 13C NMR (150 MHz, CD3OD) δ 214.6, 132.5, 125.4, 95.4, 81.9, 79.3, 75.0, 73.7, 72.9, 68.7, 63.0, 57.4, 57.4, 57.1, 56.2, 42.4, 41.8, 40.7, 40.0, 39.9, 39.4, 38.8, 35.4, 33.2, 28.6, 27.9, 25.9, 24.9, 24.6, 23.8, 19.5, 17.7, 17.0, 16.7, 16.6, 16.0. MALDI-HRMS calcd for C36H60NaO8 [M+Na]+643.4180, found 643.4185.

Example 8 3β-hydroxyl-20(S)—O-β-D-xylopyranosyl dammarane-24-ene-12-one (IE)

White solid, 4.5 g, two-step yield is 63.4%. 1H NMR (400 MHz, CD3OD) δ 5.08 (t, J=6.4 Hz, 1H), 4.39 (d, J=7.3 Hz, 1H, H-1'), 3.77 (dd, J=11.2, 5.2 Hz, 1H), 3.49-3.42 (m, 1H), 3.33 (d, J=9.4 Hz, 1H), 3.27 (t, J=8.8 Hz, 1H), 3.16-3.11 (m, 2H), 3.07 (t, J=8.8 Hz, 1H), 2.49 (dd, J=10.0, 4.4 Hz, 1H), 2.43 (t, J=13.2 Hz, 1H) 2.11 (dd, J=12.8, 2.4 Hz, 1H), 1.67 (s, 4H), 1.61 (s, 5H), 1.26 (s, 3H), 1.09 (s, 3H), 0.97 (s, 6H), 0.79 (s, 3H), 0.74 (s, 3H); 13C NMR (150 MHz, CD3OD) δ 215.5, 132.1, 125.8, 98.9, 82.4, 79.3, 78.4, 75.5, 71.3, 66.5, 57.5, 57.2, 57.1, 56.3, 42.9, 41.9, 40.7, 40.7, 40.0, 39.9, 38.8, 35.6, 33.0, 28.6, 27.9, 25.9, 24.9, 24.7, 23.0, 19.5, 17.7, 17.1, 16.7, 16.3, 16.0. MALDI-HRMS calcd for C35H58NaO7 [M+Na]+613.4075, found 613.4078.

Example 9 3β-hydroxyl-20(S)—O-α-L-rhamnopyranosyl dammarane-24-ene-12-one (IF)

White solid, 4.8 g, two-step yield is 66.7%. 1H NMR (400 MHz, (CD3)2SO) δ 5.05 (t, J=6.4 Hz, 1H), 4.78 (s, 1H), 4.74 (s, 1H), 4.60 (s, 1H), 4.50 (s, 1H), 4.35 (s, 1H), 3.55-3.48 (m, 2H), 3.44 (d, J=8.4 Hz, 1H), 3.15 (t, J=9.2 Hz, 1H), 2.98 (m, 1H), 2.94 (d, J=9.2 Hz, 1H), 2.36 (t, J=12.8 Hz, 2H), 1.64 (s, 4H), 1.57 (s, 3H), 1.14 (s, 3H), 1.07 (d, J=6.4 Hz, 3H), 0.96 (s, 3H), 0.89 (s, 3H), 0.88 (s, 3H), 0.70 (s, 3H), 0.66 (s, 3H); 13C NMR (150 MHz, (CD3)2SO) δ 201.4, 130.5, 124.6, 94.0, 79.9, 76.5, 72.2, 72.0, 71.0, 68.6, 55.3, 55.3, 55.1, 53.9, 40.7, 38.9, 38.6, 38.1, 37.1, 33.9, 31.7, 28.1, 27, 25.5, 23.7, 23.1, 21.0, 18.1, 17.9, 17.45, 16.4, 15.7, 15.7, 15.3. MALDI-HRMS calcd for C37H62NaO6 [M+Na]+ 625.4439, found 625.4444.

Example 10 3-β-methoxyl-20(S)—O-β-D-glucopyranosyl dammarane-24-ene-12-one (IG)

10.1 Synthesis of 3-β-hydroxyl-20(S)-hydroxyl dammarane-24-ene-12-one (I-4)

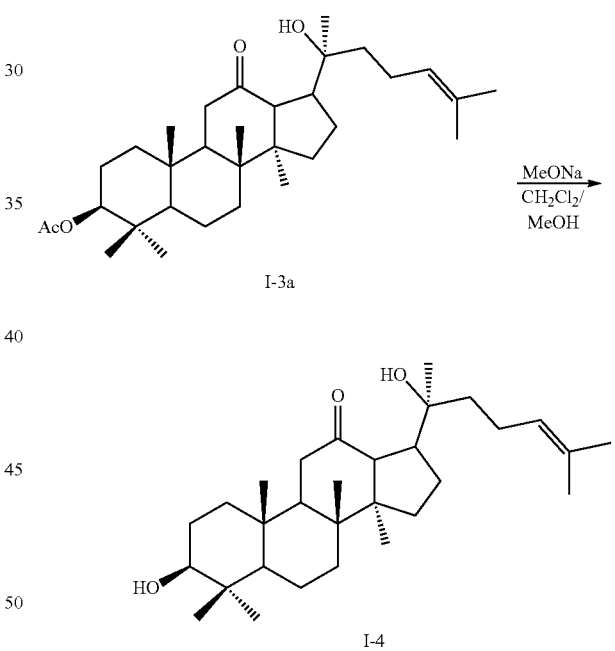

Compound I-3a (16.0 g, 31.96 mmol) was dissolved in 80.0 mL of CH2Cl2, 80.0 mL of methanol was added, and then sodium methoxide was added to make pH=9-10. The reaction was allowed to take place under 50° C. for 6.0 h and detected through TLC until it was completed. Cation resin was added to neutralize the reaction solution, and after filtration, concentration and column chromatography, light yellow solid I-4 (14.1 g, 96.2%) was obtained. 1H NMR (400 MHz, CDCl3) δ 5.10 (s, 1H), 3.20 (d, J=9.0 Hz, 1H), 2.85 (d, J=10.3 Hz, 1H), 2.40 (q, J=9.0 Hz, 1H), 2.28 (d, J=13.6 Hz, 1H), 2.21 (t, J=14.4 Hz, 1), 1.68 (s, 3H), 1.62 (s, 3H), 1.17 (s, 3H), 1.11 (s, 3H), 0.99 (s, 3H), 0.93 (s, 3H), 0.80 (s, 6H).

10.2 Synthesis of 3-β-methoxyl-20(S)-hydroxyl dammarane-24-ene-12-one (I-5a)

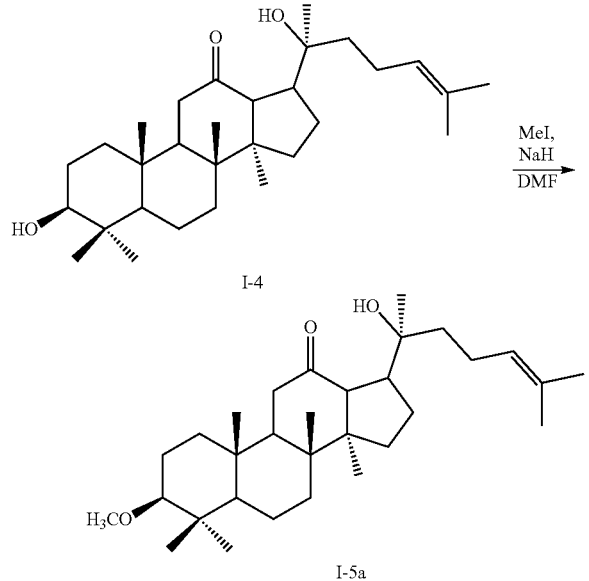

I-4 (7.3 g, 15.91 mmol) was dissolved in dried DMF (200.0 mL), iodomethane (1.99 mL, 31.96 mmol) was added, 60% sodium hydride (1.9 g, 47.94 mmol) was added in batch under ice bath, and the reaction was allowed to take place at room temperature. After the reaction, water was slowly dripped to quench the reaction, diluted with ethyl acetate, washed successively with 1 mol/L hydrochloric acid, saturated sodium bicarbonate and saturated sodium chloride, the organic layer was dried with anhydrous sodium sulfate, concentrated under reduced pressure, and separated with column chromatography (EA/PE, 1:6), and light yellow liquid I-5a (5.9 g, 78.4%) was obtained. 1H NMR (400 MHz, CDCl3) δ 5.61 (s, 1H), 5.06 (t, J=7.1 Hz, 1H), 3.52 (s, 3H), 3.23 (dd, J=11.0, 4.4 Hz, 1H), 2.94-2.86 (m, 1H), 1.66 (s, 3H), 1.60 (s, 3H), 1.17 (s, 3H), 1.00 (s, 3H), 0.99 (s, 3H), 0.97 (s, 3H), 0.84 (s, 3H), 0.80 (s, 3H); 13C NMR (150 MHz, CDCl$_3$) δ 214.3, 142.7, 125.7, 79.0, 74.5, 55.8, 55.2, 54.0, 52.4, 48.9, 39.0, 38.9, 38.5, 37.3, 36.7, 34.6, 31.6, 28.3, 28.2, 27.3, 26.8, 25.9, 25.2, 22.7, 22.2, 18.3, 17.9, 16.9, 15.8, 15.7.

10.3 3-β-methoxyl-20(S)—O-β-D-glucopyranosyl dammarane-24-ene-12-one (IG)

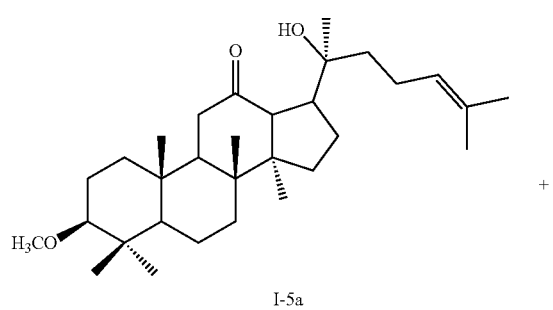

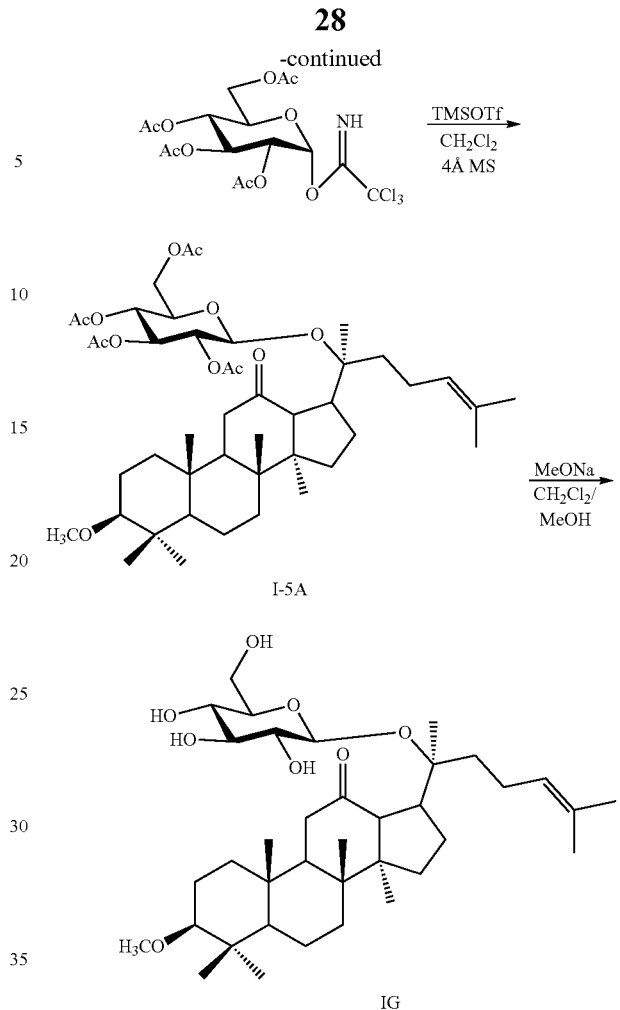

I-5a (5.8 g, 12.27 mmol) and 2,3,4,6-tetra-O-acetyl glucosamine trichloroimine ester (9.1 g, 18.41 mmol) were dissolved in dried CH2Cl2, appropriate amount of 4 Å molecular sieve was added, protected by argon, stirred for 30 min at room temperature, then the temperature of the reaction system was reduced to −40° C., and TMSOTf (222.3 μL, 1.23 mmol) was dripped for reaction at −40° C. After the reaction was detected through TLC until it was completed, Et3N was added to stop the reaction and the mixture was restored to room temperature. The molecular sieve was removed by suction filtration, and the reaction solution was concentrated into solid. The concentrate was dissolved in a mixed solvent of dichloromethane and methanol (150.0 mL, v:v=1:1), sodium methoxide was added to make pH=9-10, then reaction for 1.0 h at room temperature. The reaction was detected through TLC until it was completed. Cation resin was added to neutralize the reaction solution, and after filtration, concentration and column chromatography, white solid IG (4.0 g, 52.0% two-step yield) was obtained. 1H NMR (400 MHz, CD3OD) δ 5.09 (t, J=6.7 Hz, 1H), 4.48 (d, J=7.6 Hz, 1H), 3.81 (d, J=11.3 Hz, 1H), 3.64 (dd, J=11.8, 7.6 Hz, 1H), 3.48 (s, 3H), 3.38 (t, J=8.9 Hz, 1H), 3.23-3.14 (m, 4H), 3.09-3.07 (m, 1H), 2.18-1.95 (m, 5H), 1.66 (s, 3H), 1.62 (s, 3H), 1.33 (s, 3H), 1.03 (s, 3H), 1.00 (s, 3H), 0.97 (s, 3H), 0.88 (s, 3H), 0.79 (s, 3H).

Example 11 20(S)—O-β-D-glucopyranosyl dammarane-3, 24-diene-12-one (IH, i.e. RSM-17)

11.1 Synthesis of 3-β-O-p-toluene sulfonyl-20(S)-hydroxyl dammarane-24-ene-12-one (I-6)

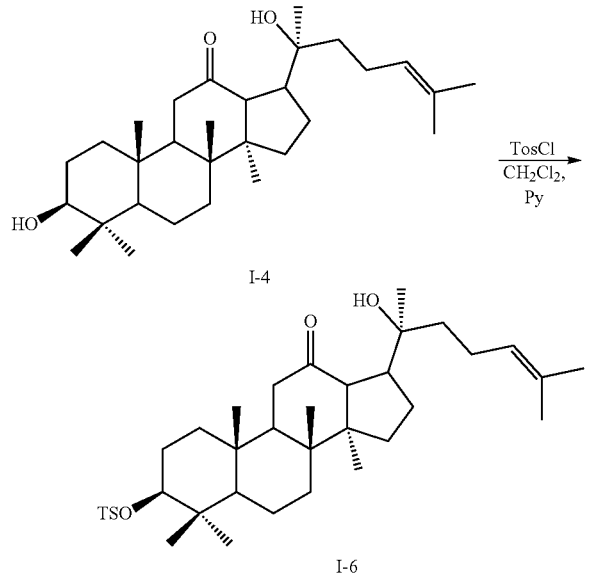

I-4 (3.3 g, 7.19 mmol) was dissolved in dried CH2Cl2 and pyridine, p-toluenesulfonyl chloride (13.7 g, 71.90 mmol) was added under ice bath, and the reaction was allowed to take place at 80° C. for 6.0 h. After the reaction, water was slowly dripped to quench the reaction, diluted with ethyl acetate, washed successively with 1 mol/L hydrochloric acid, saturated sodium bicarbonate and saturated sodium chloride, the organic layer was dried with anhydrous sodium sulfate, concentrated under reduced pressure, and separated with column chromatography, and white solid I-6 (3.8 g, 87.5%) was obtained. 1H NMR (400 MHz, CDCl3) δ 7.79 (d, J=7.3 Hz, 2H), 7.33 (d, J=7.4 Hz, 2H), 5.09 (s, 1H), 4.18 (d, J=11.2 Hz, 1H), 3.18 (s, 1H), 2.83 (d, J=10.0 Hz, 1H), 2.44 (s, 3H), 2.41-2.34 (m, 1H), 2.20 (d, J=11.2 Hz, 2H), 1.68 (s, 3H), 1.61 (s, 3H), 1.15 (s, 3H), 1.10 (s, 3H), 0.90 (s, 3H), 0.83 (s, 6H), 0.77 (s, 3H); 13C NMR (150 MHz, CDCl$_3$) δ 213.8, 144.5, 134.9, 131.7, 129.8, 127.8, 125.0, 90.3, 73.3, 56.3, 56.0, 54.8, 53.3, 46.2, 40.3, 39.3, 38.8, 38.4, 38.0, 37.3, 33.9, 30.9, 28.0, 26.5, 25.9, 24.8, 24.6, 22.6, 21.8, 18.5, 17.8, 17.6, 16.3, 16.0, 15.9. MALDI-HRMS calcd for C37H57O5S [M+H]+ 613.3921, found 613.3927.

11.2 Synthesis of 20(S)-hydroxyl dammarane-3, 24-diene-12-one (I-7)

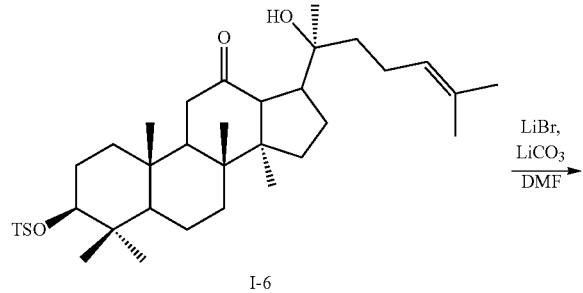

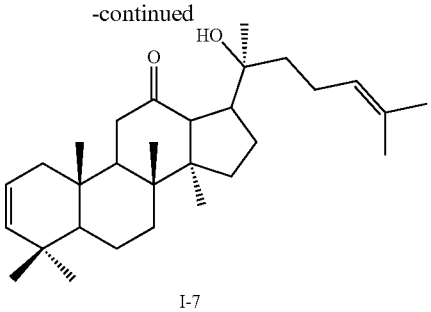

I-6 (3.8 g, 6.20 mmol) was dissolved in DMF (50.0 mL), lithium bromide (5.2 g, 49.60 mmol) and lithium carbonate (3.7 g, 49.60 mmol) were added. the reaction was allowed to take place under 153° C. for 1.5 h. The reaction solution was cooled to room temperature, water was added to stop the reaction, diluted with ethyl acetate, washed successively with 1 mol/L hydrochloric acid, saturated sodium bicarbonate and saturated sodium chloride, the organic layer was dried with anhydrous sodium sulfate, concentrated under reduced pressure, and separated with column chromatography(EA/PE, 1:6), I-7 (2.3 g, 84.2%) was obtained. 1H NMR (400 MHz, CDCl3) δ 5.40 (s, 2H), 5.11 (s, 1H), 2.89 (d, J=9.9 Hz, 1H), 2.42 (s, 1H), 2.32-1.96 (m, 5H), 1.69 (s, 3H), 1.62 (s, 3H), 1.21 (s, 3H), 1.13 (s, 3H), 0.96 (s, 6H), 0.92 (s, 3H), 0.81 (s, 3H); 13C NMR (150 MHz, CDCl3) δ 214.4, 138.2, 131.6, 125.0, 121.1, 73.3, 56.3, 55.1, 52.5, 52.4, 46.2, 40.9, 40.4, 39.4, 37.9, 36.8, 34.8, 33.3, 31.8, 30.9, 26.5, 25.9, 24.8, 22.7, 22.6, 19.6, 17.8, 17.5, 16.2, 15.5. MALDI-HRMS calcd for C30H48NaO2 [M+Na]+463.3547, found 463.3543.

11.3 20(S)—O-β-D-glucopyranosyl dammarane-3, 24-diene-12-one (IH)

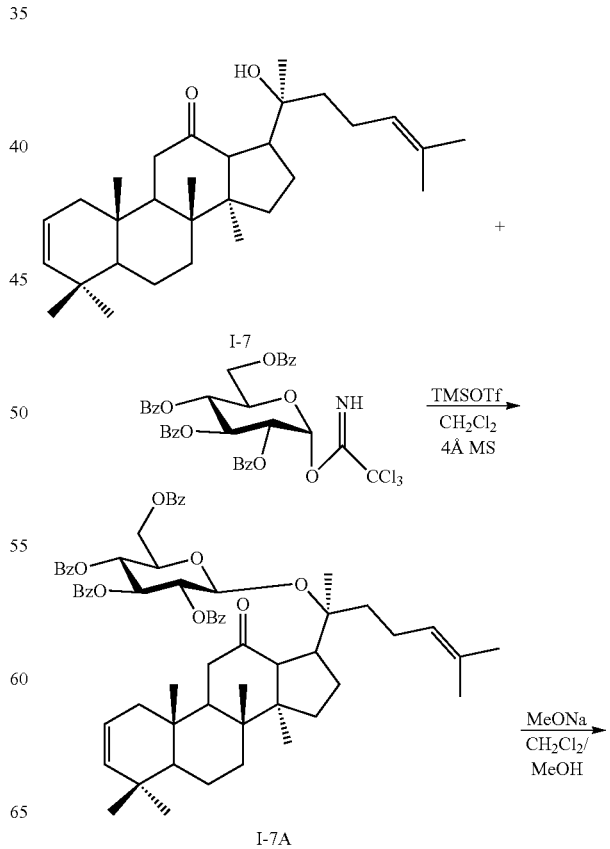

-continued

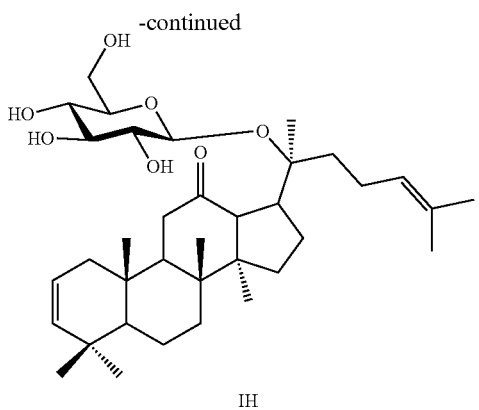

IH

I-7 (2.3 g, 5.22 mmol) and 2,3,4,6-tetra-O-benzoyl glucose trichloroimine ester (4.6 g, 6.26 mmol) were dissolved in dried CH2Cl2 (60.0 mL), and appropriate amount of 4 Å molecular sieve was added, protected by argon. It was stirred for 30 min at room temperature, then the temperature of the reaction system was reduced to −40° C., and TMSOTf (94.3 μL, 0.52 mmol) was dripped and the reaction was allowed to take place under −40° C. After the reaction was detected through TLC until it was completed, Et3N was added to stop the reaction, the reaction system was restored to room temperature, the molecular sieve was removed by suction filtration, and the reaction solution was concentrated into solid. The concentrate was dissolved in a mixed solvent of dichloromethane and methanol (50.0 mL, v:v=1:1), sodium methoxide was added to make pH=9-10, then reaction was allowed to take place for 4.0 h at room temperature. The reaction was detected through TLC until it was completed. Cation resin was added to neutralize the reaction solution, and after filtration, concentration and column chromatography, white solid IH (2.5 g, 79.5% two-step yield) was obtained. 1H NMR (400 MHz, CD3OD) δ 5.44-5.36 (m, 2H), 5.09 (t, J=6.6 Hz, 1H), 4.44 (d, J=7.6 Hz, 1H), 3.80 (dd, J=11.7, 1.5 Hz, 1H), 3.65 (dd, J=11.7, 5.5 Hz, 1H), 3.37-3.34 (m, 2H), 3.28 (t, J=8.8 Hz, 1H), 3.20 (dd, J=8.3, 6.0 Hz, 1H), 3.10 (t, J=8.1 Hz, 1H), 2.54-2.45 (m, 2H), 2.08 (dd, J=12.8, 3.2 Hz, 1H), 1.66 (s, 3H), 1.62 (s, 3H), 1.30 (s, 3H), 1.12 (s, 3H), 1.00 (s, 3H), 0.97 (s, 3H), 0.93 (s, 3H), 0.76 (s, 3H); 13C NMR (150 MHz, CD3OD) δ 215.5, 139.2, 131.9, 126.0, 122.2, 98.3, 82.5, 78.7, 77.4, 75.6, 71.7, 62.9, 57.8, 57.1, 55.1, 53.9, 42.9, 42.2, 41.9, 40.8, 40.7, 38.0, 35.7, 34.8, 33.0, 32.1, 25.9, 24.9, 24.7, 23.0, 22.9, 20.7, 17.8, 17.1, 16.9, 15.7. MALDI-HRMS calcd for C36H58NaO7 [M+Na]+ 625.4075, found 625.4080.

Example 12
20-O-β-D-xylopyranosyl-20(S)-panaxadiol glycoside(IJ)

White solid. 1H NMR (CD3OD): 5.09 (t, J=7.1 Hz, 1H, H-24), 4.52 (d, J=7.7 Hz, 1H, H-1'), 3.78 (dd, J=11.5, 5.5 Hz, 1H, H-5'-2), 3.68 (td, J=10.4, 4.9 Hz, 1H, H-12), 3.45 (ddd, J=10.4, 8.8, 5.5 Hz, 1H, H-4'), 3.29 (t, J=8.8 Hz, 1H, H-3'), 3.14 (dd, J=11.5, 10.4 Hz, 1H, H-5'-1), 3.13 (dd, J=11.0, 4.4 Hz, 1H, H-3), 3.07 (dd, J=8.8, 7.7 Hz, 1H, H-12), 1.67 (s, 3H), 1.61 (s, 3H), 1.32 (s, 3H), 1.00 (s, 3H), 0.96 (s, 3H), 0.91 (s, 3H), 0.90 (s, 3H), 0.70 (s, 3H); 13C NMR (CDCl3): 132.3 (C-25), 128.2 (C-24), 98.9 (C-1'), 84.8 (C-20), 79.6 (C-3), 78.4 (C-3'), 75.3 (C-2'), 71.8 (C-12), 71.1 (C-4'), 66.8 (C-5'), 57.3, 53.1, 52.4, 51.0, 40.9, 40.2, 40.0, 38.1, 36.7, 35.9, 31.5, 30.8, 28.6, 28.0, 27.2, 25.9, 23.9, 22.4, 19.4, 18.3, 17.8, 17.3, 16.7, 16.3, 16.1.

Example 13
20-O-β-L-rhamnopyranosyl-20(S)-panaxadiol glycoside(IK)

White solid. 1H NMR (CD3OD): 5.13 (d, J=1.4 Hz, 1H, H-1'), 5.13 (t, J=7.1 Hz, 1H, H-24), 3.79 (m, 1H, H-2'), 3.79 (m, 1H, H-5'), 3.60 (td, J=10.1, 5.5 Hz, 1H, H-12), 3.56 (dd, J=9.6, 3.2 Hz, 1H, H-3'), 3.38 (t-like, J=9.6, 9.2 Hz, 1H, H-4), 3.13 (dd, J=11.5, 4.6 Hz, 1H, H-3), 1.69 (s, 3H), 1.62 (s, 3H), 1.36 (s, 3H), 1.24 (d, J=6.0 Hz, 3H, H-5'), 1.00 (s, 3H), 0.96 (s, 3H), 0.93 (s, 3H), 0.91 (s, 3H), 0.77 (s, 3H); MS: 629[M+Na]+, 607[M+H]+, 589.5[M-OH]+, 443.4, 425.4, 407.4.

Example 14
20-O-α-L-arabinopyrauosyl-20(S)-panaxadiol glycoside (IL)

White solid. 1H NMR (CD3OD): 5.10 (d, J=7.3 Hz, 1H, H-24), 4.50 (d, J=7.3 Hz, 1H, H-1), 3.84 (dd, J=12.4, 1.4 Hz, 1H, H-5'-1), 3.79 (brs, 1H, H-4'), 3.71 (td, J=10.6, 5.5 Hz, 1H, H-12), 3.53 (dd, J=12.4, 1.4 Hz, 1H, H-5'-2), 3.51 (dd, J=6.4, 3.2 Hz, 1H, H-3'), 3.45 (dd, J=9.1, 7.3 Hz, 1H, H-2'), 3.14 (dd, J=11.5, 4.6 Hz, 1H, H-3), 1.67 (s, 3H), 1.62 (s, 3H), 1.34 (s, 3H), 1.01 (s, 3H), 0.96 (s, 3H), 0.92 (s, 3H), 0.91 (s, 3H), 0.78 (s, 3H).

Example 15 Synthesis of 16 20(S)—O-β-D-glucopyranosyl dammarane-24-ene-3, 12-dione (IIA) and 20(S)-hydroxyl-3-O-β-D-glucopyranosyl dammarane-3, 24-diene-12-one (IIA-1)

15.1 Synthesis of 20(S)-hydroxyl dammarane-24-ene-3, 12-dione (II-1)

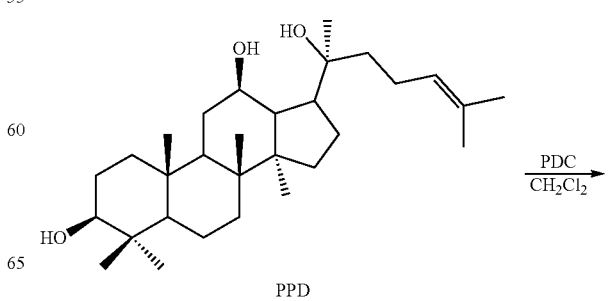

PPD

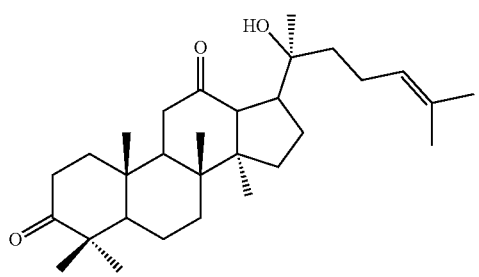

II-1

PPD (40.0 g, 86.82 mmol) was dissolved in dried dichloromethane (500.0 mL), PDC (98.0 g, 260.46 mmol) and acetic anhydride (32.8 mL, 347.28 mmol) were added, reaction was allowed to take place for 5.0 h at room temperature, insoluble substance was removed through suction filtration, filtrate was concentrated and separated by column chromatography(EA/PE, 1:8), and light yellow foamed solid II-1 (24.3 g, 61.2%) was obtained. 1H NMR (400 MHz, CDCl3) δ 5.11 (t, J=7.1 Hz, 1H, H-24), 2.90 (d, J=9.6 Hz, 1H, H-13), 2.55-2.40 (m, 3H), 2.29 (d, J=7.7 Hz, 2H), 1.69 (s, 3H), 1.62 (s, 3H), 1.23 (s, 3H), 1.11 (s, 6H) 1.07 (s, 3H), 1.04 (s, 3H), 0.81 (s, 3H).

15.2 Synthesis of 20(S)—O-β-D-glucopyranosyl dammarane-24-ene-3, 12-dione (2A) and 20(S)-hydroxyl-3-O-β-D-glucopyranosyl dammarane-3, 24-diene-12-one (2A-1)

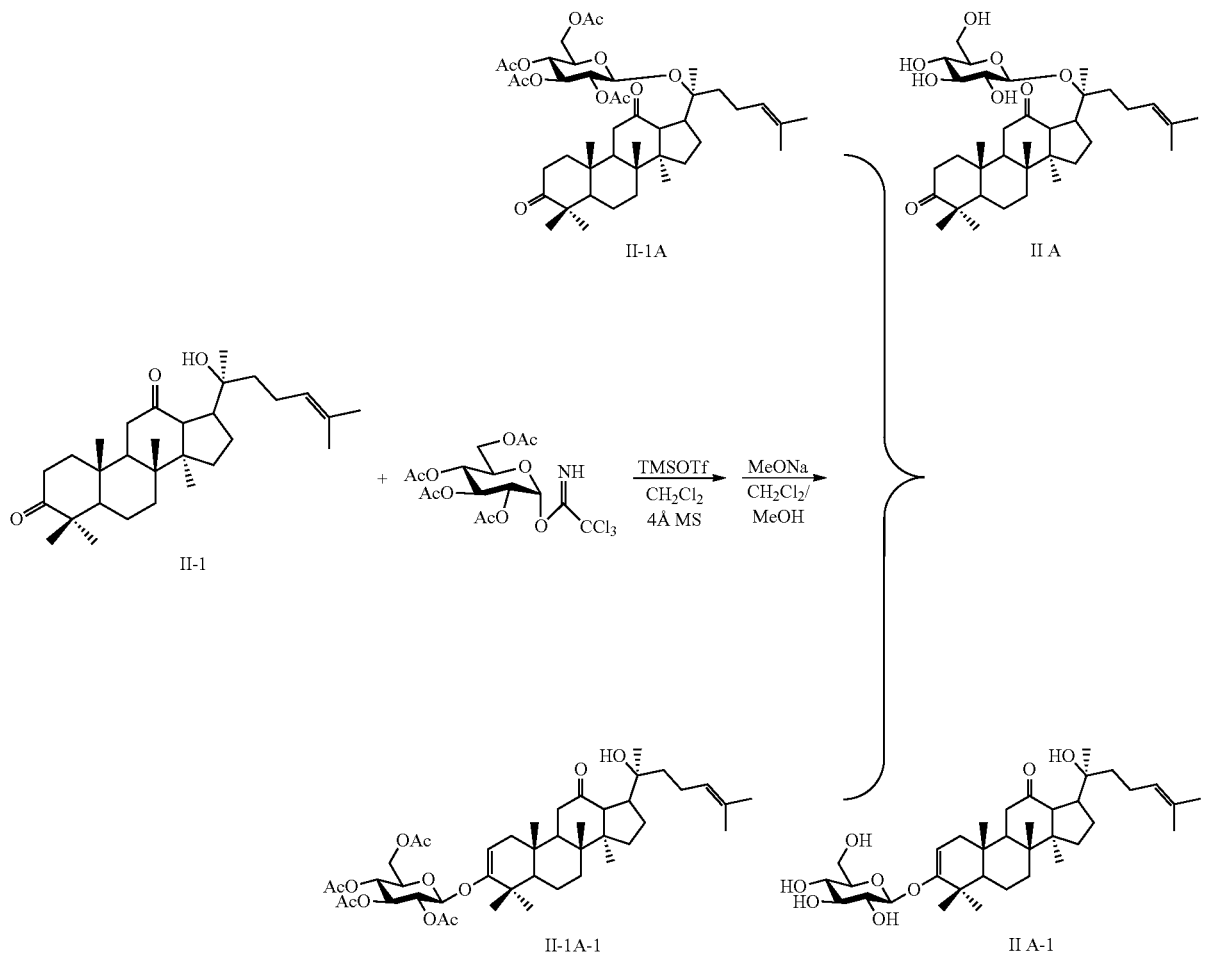

II-1 (11.0 g, 24.08 mmol) and 2,3,4,6-tetra-O-acetyl glucose trichloroimine ester (17.8 g, 36.12 mmol) were dissolved in dried CH2Cl2, and appropriate amount of 4 Å molecular sieve was added, protected by argon. It was stirred for 30 min at room temperature, then the temperature of the reaction system was reduced to −40° C., and TMSOTf (435.5 μL, 2.41 mmol) was dripped for reaction at −40° C. After the reaction was detected through TLC until it was completed, Et3N was added to stop the reaction, the reaction system was restored to room temperature, the molecular sieve was removed through suction filtration, and the reaction solution was concentrated into solid. The concentrate was dissolved in a mixed solvent of dichloromethane and methanol (150.0 mL, v:v=1:1), sodium methoxide was added to make pH=9-10, and then reaction was allowed to take place for 1.0 h at room temperature. The reaction was detected through TLC until it was completed. Cation resin was added to neutralize the reaction solution, and after filtration, concentration and column chromatography, white solid IIA (5.8 g, 38.9% two-step yield) and IIA-1 (5.6 g, 37.6% two-step yield) were obtained. IIA: 1H NMR (400 MHz, CD3OD) δ 5.10 (t, J=6.4 Hz, 1H), 4.45 (d, J=7.7 Hz, 1H), 3.80 (dd, J=11.8, 1.4 Hz, 1H), 3.65 (dd, J=11.7, 5.4 Hz, 1H), 3.40-3.33 (m, 2H), 3.28 (d, J=8.9 Hz, 1H), 3.21 (dd, J=7.4, 5.1 Hz, 1H), 3.11 (t, J=8.2 Hz, 1H), 2.54-2.48 (m, 4H), 2.14 (dd, J=12.8, 3.2 Hz, 1H), 1.67 (s, 3H), 1.62 (s, 3H), 1.31 (s, 3H), 1.12 (s, 3H), 1.09 (s, 3H), 1.07 (s, 6H), 0.77 (s, 3H); 13C NMR (150 MHz, CD3OD) δ 220.0, 214.8, 131.9, 126.0, 98.3, 82.5, 78.8, 77.4, 75.6, 71.8, 62.9, 57.5, 57.2, 56.1, 55.4, 43.0, 41.8, 40.8, 40.7, 40.3, 38.5, 34.8, 33.0, 27.1, 25.9, 24.9, 24.7, 22.9, 21.4, 20.9, 17.8, 17.1, 16.3, 15.8. MALDI-HRMS calcd for C36H58NaO8 [M+Na]+ 641.4024, found 625.4041.

IIA-1:1H NMR (400 MHz, CD3OD) δ 5.09 (t, J=6.7 Hz, 1H), 4.94 (d, J=7.3 Hz, 1H), 4.59 (d, J=8.1 Hz, 1H), 3.83 (d, J=12.2 Hz, 1H), 3.66 (dd, J=12.1, 4.7 Hz, 1H), 3.39-3.29 (m, 3H), 3.07 (d, J=9.5 Hz, 1H), 2.46-2.35 (m, 2H), 2.14 (d, J=14.8 Hz, 1H), 2.06-1.92 (m, 3H), 1.66 (s, 3H), 1.61 (s, 3H), 1.27 (s, 3H), 1.15 (s, 3H), 1.01 (s, 6H), 0.99 (s, 3H), 0.77 (s, 3H); 13C NMR (150 MHz, CD3OD) δ 215.2, 160.6, 132.1, 125.8, 102.1, 97.2, 78.3, 77.9, 75.1, 75.0, 71.4, 62.5, 57.5, 57.3, 55.0, 54.6, 44.4, 42.1, 41.6, 40.7, 40.6, 38.6, 37.6, 34.7, 32.7, 28.8, 25.9, 25.7, 24.9, 23.9, 20.6, 20.0, 17.7, 17.3, 16.4, 15.7. MALDI-HRMS calcd for C36H58NaO8 [M+Na]+641.4024, found 625.4040.

Example 17 20(S)—O-β-D-glucopyranosyl dammarane-1, 24-diene-3, 12-dione (IIB)

17.1 Synthesis of 20(S)-hydroxyl dammarane-1, 24-diene-3, 12-dione (II-2)

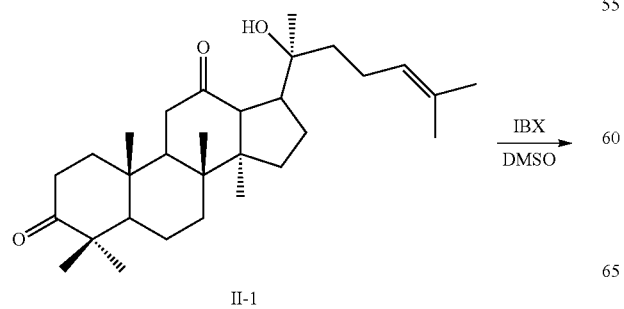

II-1

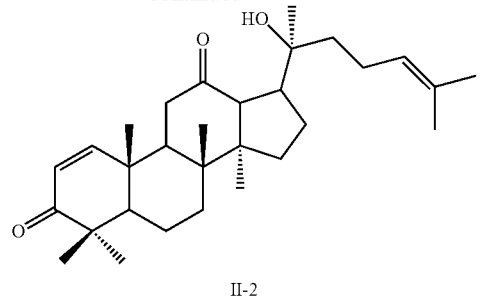

II-2

I-1 (12.0 g, 26.27 mmol) was dissolved in DMSO (88.0 mL), and IBX (24.0 g, 39.41 mmol) was added. The reaction was allowed to take place under 70° C. for 24.0 h. The reaction solution was cooled to room temperature, water was added to stop the reaction, diluted with ethyl ether, washed successively with saturated sodium bicarbonate and saturated sodium chloride, the organic layer was dried with anhydrous sodium sulfate, concentrated under reduced pressure, and separated with column chromatography (EA/PE, 1:7), 11-2 (8.4 g, 70.5%) was obtained. 1H NMR (400 MHz, CDCl3) δ 6.98 (d, J=10.0 Hz, 1H), 5.81 (d, J=9.9 Hz, 1H), 5.07 (s, 1H), 2.88 (d, J=10.8 Hz, 1H), 2.47 (d, J=13.8 Hz, 1H), 2.38 (t, J=12.5 Hz, 2H), 1.65 (s, 3H), 1.59 (s, 3H), 1.23 (s, 3H), 1.13 (s, 6H), 1.09 (s, 6H), 0.78 (s, 3H).

17.2 Synthesis of 20(S)—O-β-D-glucopyranosyl dammarane-1, 24-diene-3, 12-dione (IIB)

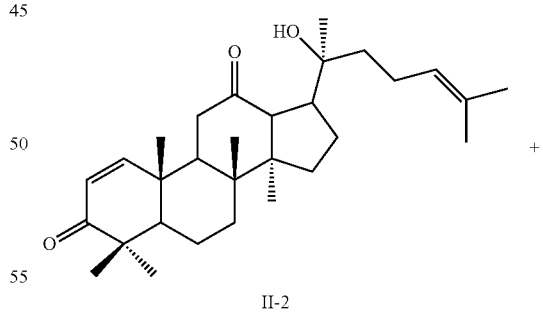

II-2

+

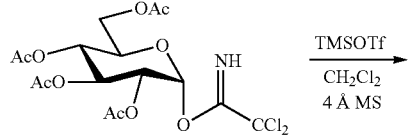

-continued

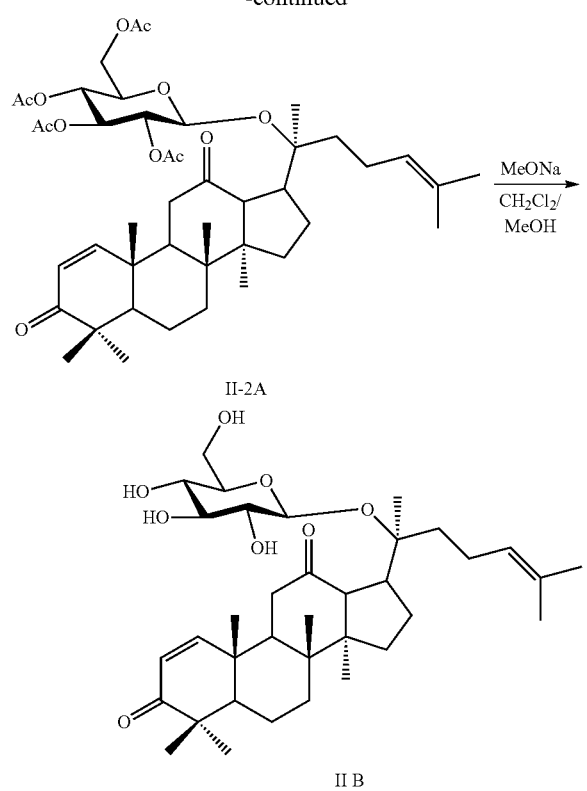

II-2A

II B

II-2 (8.3 g, 18.25 mmol) and 2,3,4,6-tetra-O-acetyl glucose trichloroimine ester (13.5 g, 27.37 mmol) were dissolved in dried CH2Cl2, appropriate amount of 4 Å molecular sieve was added, protected by argon, stirred for 30 min at room temperature, then the temperature of the reaction system was reduced to −40° C., and TMSOTf (330.7 μL, 1.83 mmol) was dripped for reaction at −40° C. After the reaction was detected through TLC until it was completed, Et3N was added to stop the reaction, the reaction system was restored to room temperature, the molecular sieve was removed by suction filtration, and the reaction solution was concentrated into solid. The concentrate was dissolved in a mixed solvent of dichloromethane and methanol (100.0 mL, v:v=1:1), sodium methoxide was added to make pH=9-10, and then reaction was allowed to take place for 1.0 h at room temperature. The reaction was detected through TLC until it was completed. Cation resin was added to neutralize the reaction solution, and after filtration, concentration and column chromatography, white solid 2B (5.1 g, 45.3% two-step yield) was obtained. 1H NMR (400 MHz, CD3OD) δ 7.21 (d, J=10.1 Hz, 1H), 5.81 (d, J=10.1 Hz, 1H), 5.10 (t, J=6.3 Hz, 1H), 4.45 (d, J=7.4 Hz, 1H), 3.80 (d, J=12.0 Hz, 1H), 3.65 (dd, J=12.0, 4.9 Hz, 1H), 3.40 (d, J=9.7 Hz, 1H), 3.35 (t, J=9.2 Hz, 1H), 3.27 (d, J=9.6 Hz, 1H), 3.22-3.19 (m, 1H), 3.11 (t, J=7.9 Hz, 1H), 2.64 (t, J=13.0 Hz, 1H), 2.54-2.49 (m, 2H), 2.39 (d, J=12.4 Hz, 1H), 1.66 (s, 3H), 1.62 (s, 3H), 1.35 (s, 3H), 1.21 (s, 3H), 1.14 (s, 6H), 1.11 (s, 4H), 0.76 (s, 3H); 13C NMR (150 MHz, CD3OD) δ 213.8, 207.3, 160.6 131.9, 126.1, 126.0, 98.3, 82.4, 78.7, 77.4, 75.6, 71.7, 62.8, 57.3, 55.0, 50.1, 45.9, 42.9, 42.7, 41.3, 40.7, 40.4, 34.9, 32.8, 28.1, 25.9, 24.9, 24.7, 22.9, 21.8, 20.2, 19.7, 17.8, 17.1, 16.5. MALDI-HRMS calcd for C36H56NaO8 [M+Na]+639.3867, found 639.3873.

Example 18 20(S)—O-β-D-glucopyranosyl dammarane-3-methoxy imino-24-ene-12-one (IIIA)

18.1 Synthesis of 3-β-hydroxyl-12-β-O-trimethylacetyl-20(S)-panaxadiol glycoside

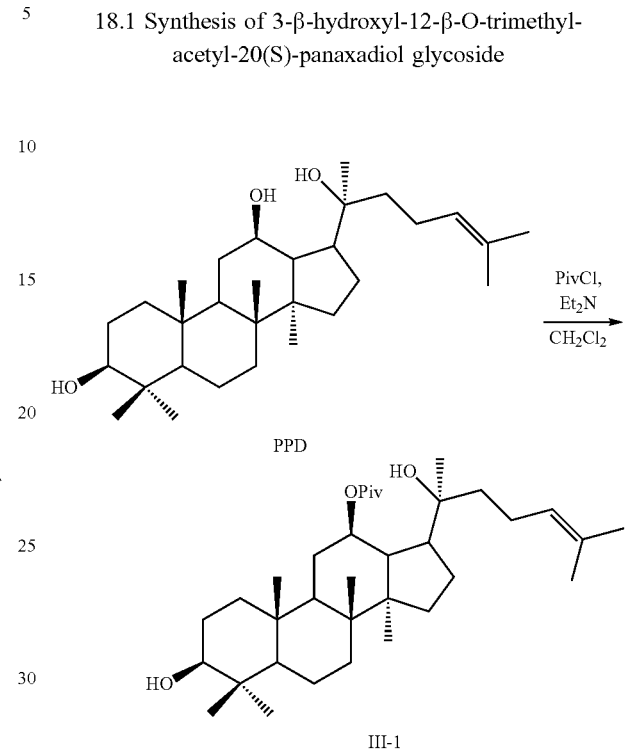

PPD

III-1

PPD (45.0 g, 97.68 mmol) was dissolved in 500.0 mL of dichloromethane, triethylamine (27.1 mL, 195.36 mmol) was added, the temperature of the reaction system was reduced to −5° C., and trimethylacetyl chloride (24.1 mL, 195.36 mmol) was dripped under ice bath. The reaction was allowed to take place for 3.0 h at −5° C. Water was added to stop the reaction, washed successively with water and saturated sodium chloride, the organic layer was dried with anhydrous sodium sulfate, and concentrated under reduced pressure. 36.6 g of crude product was obtained, which was directly used for the next reaction.

18.2 Synthesis of 12-β-O-trimethylacetyl-20(S)-hydroxyl dammarane-24-ene-3-one (III-2)

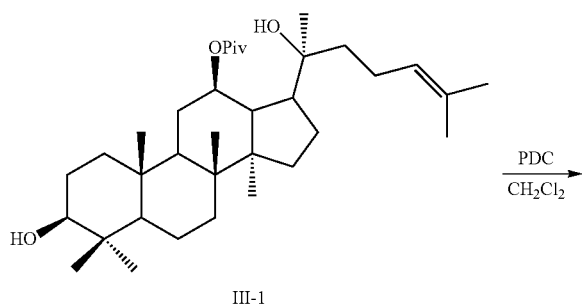

III-1

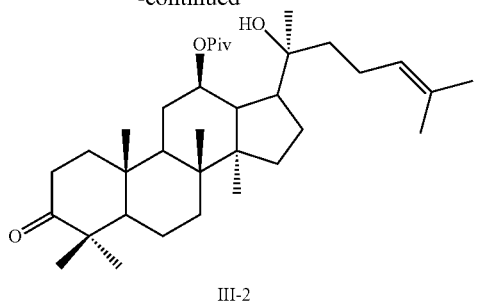

III-2

II-1 (36.6 g, 67.17 mmol) was dissolved in 600.0 mL of dried dichloromethane, PDC (37.9 g, 100.76 mmol) and acetic anhydride (19.0 mL, 201.51 mmol) were added, reacted at room temperature for about 5.0 h. The insoluble substance was removed by suction filtration. The filtrate was concentrated and directly used for the next reaction. 1H NMR (400 MHz, CDCl$_3$) δ 5.15 (t, J=7.2 Hz, 1H), 4.82 (t, J=10.4 Hz, 1H), 2.47-2.45 (m, 2H), 2.22 (s, 1H), 1.71 (s, 3H), 1.63 (s, 3H), 1.21 (s, 9H), 1.12 (s, 3H), 1.09 (s, 3H), 1.06 (s, 3H), 1.04 (s, 3H), 0.98 (s, 3H), 0.93 (s, 3H).

18.3 Synthesis of 12-β-hydroxyl-20(S)-hydroxyl dammarane-24-ene-3-one (III-3)

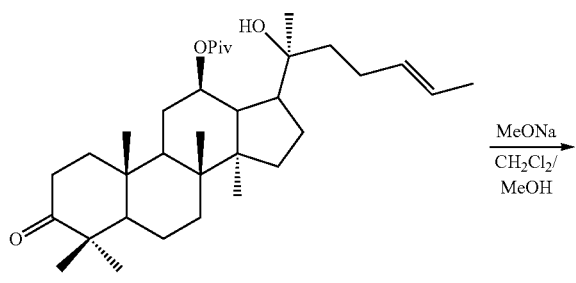

III-2

The concentrate previous-step was dissolved in the mixed solvent of dichloromethane and methanol (400.0 mL, v:v=1:1), sodium methoxide was added to make pH=9-10, and then reaction was allowed to take place for 6.0 h at 50° C. The reaction was detected through TLC until it was completed. Cation resin was added to neutralize the reaction solution, and after filtration, concentration and column chromatography, white solid III-3 (17.9 g, 39.9% three-step yield) was obtained. 1H NMR (400 MHz, CDCl3) δ 5.16 (s, 1H, H-24), 3.62-3.57 (m, 1H, H-3), 2.54-2.41 (m, 2H), 1.70 (s, 3H), 1.64 (s, 3H), 1.20 (s, 3H), 1.08 (s, 3H), 1.04 (s, 3H), 1.03 (s, 3H), 0.98 (s, 3H), 0.89 (s, 3H).

18.4 Synthesis of 12-β-hydroxyl-20(S)-hydroxyl dammarane-3-methoxy imino-24-ene (III-4a)

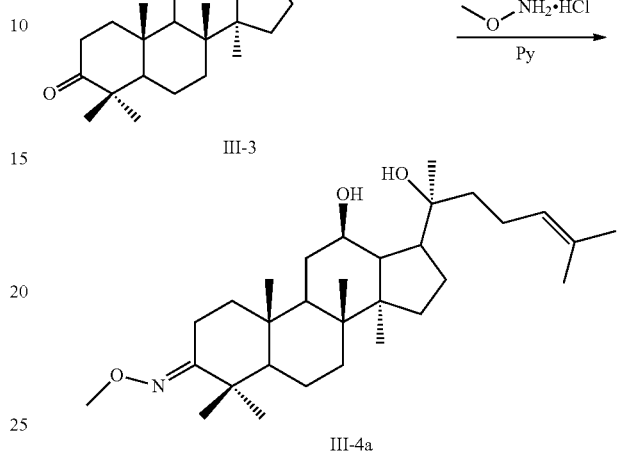

III-3 (2.3 g, 5.01 mmol) was dissolved in pyridine (60.0 mL), and O-methyl hydroxylamine hydrochloride (628.1 mg, 7.52 mmol) was added. The reaction was allowed to take place under 80° C. for 4.0 h. The reaction solution was cooled to room temperature, water was added to stop the reaction, diluted with ethyl acetate, washed successively with 1 mol/L hydrochloric acid, saturated sodium bicarbonate and saturated sodium chloride, the organic layer was dried with anhydrous sodium sulfate, concentrated under reduced pressure, and directly used for the next reaction.

18.5 Synthesis of 20(S)-hydroxyl dammarane-3-methoxy imino-24-ene-12-one (III-5a)

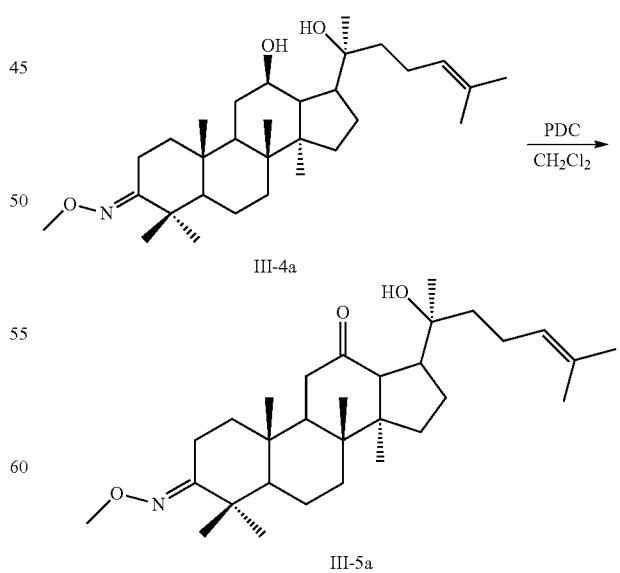

III-4a was dissolved in 120 mL of dry dichloromethane, PDC (2.8 g, 7.52 mmol) and acetic anhydride (1.4 mL, 15.03 mmol) were added. The reaction was allowed to take place under room temperature for about 5.0 h. The insoluble substance was removed by suction filtration. The filtrate was concentrated and separated by column chromatography, light yellow foamed solid III-5a (1.1 g, 45.2% two-step yield) was obtained. 1H NMR (400 MHz, CDCl3) δ 5.10 (s, 1H, H-24), 3.81 (s, 3H), 3.25 (s, 1H), 2.92 (d, J=14.8 Hz, 1H), 2.86 (d, J=10.4 Hz, 1H), 2.40 (d, J=8.0 Hz, 1H), 1.69 (s, 3H), 1.62 (s, 3H), 1.20 (s, 3H), 1.16 (s, 3H), 1.12 (s, 3H), 1.07 (s, 3H), 1.01 (s, 3H), 0.78 (s, 3H); 13C NMR (150 MHz, CDCl3) δ 214.0, 165.2, 131.7, 125.0, 73.2, 61.2, 56.4, 56.0, 54.9, 53.1, 46.2, 40.3, 40.2, 39.3, 38.5, 37.9, 37.5, 33.7, 30.9, 27.5, 26.5, 25.9, 24.8, 23.2, 22.6, 19.2, 17.8, 17.5, 15.9, 15.6. MALDI-HRMS calcd for C31H51NNaO3 [M+Na]+ 508.3761, found 508.3760.

18.6 Synthesis of 20(S)—O-β-D-glucopyranosyl dammarane-3-methoxy imino-24-ene-12-one (IIIA)

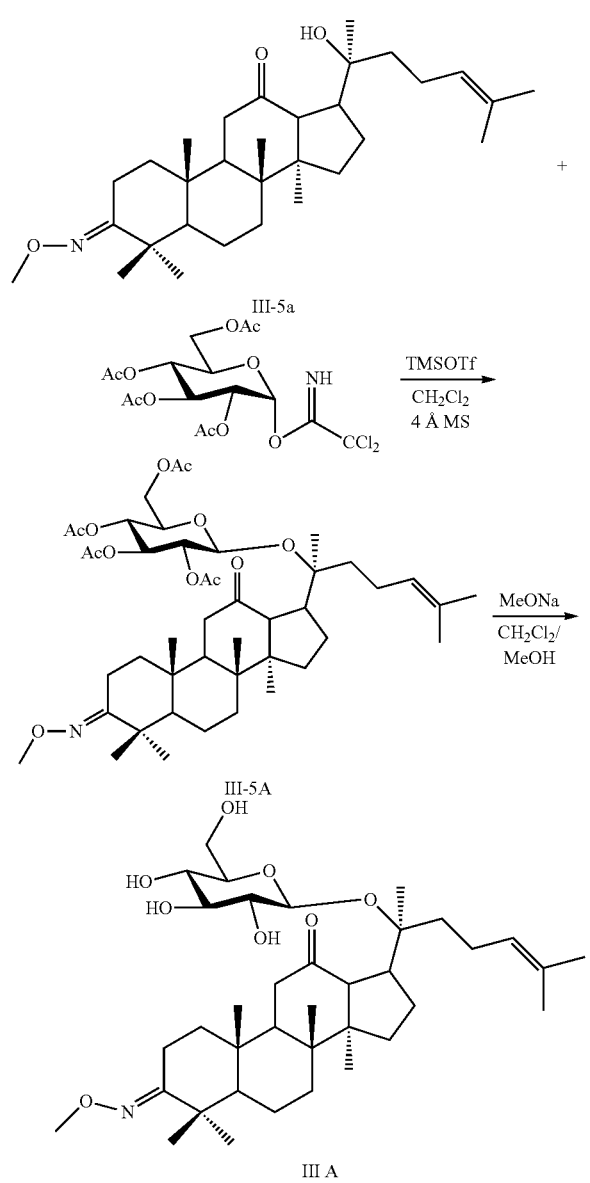

III-5a (1.1 g, 2.26 mmol) and 2,3,4,6-tetra-O-acetyl glucosamine trichloroimine ester (1.3 g, 2.71 mmol) were dissolved in dried CH2Cl2, appropriate amount of 4 Å molecular sieve was added, protected by argon, stirred for 30 min at room temperature, then the temperature of the reaction system was reduced to −40° C., and TMSOTf (40.8 μL, 0.23 mmol) was dripped for reaction at −40° C. After the reaction was detected through TLC until it was completed, Et3N was added to stop the reaction, the reaction system was restored to room temperature, the molecular sieve was removed by suction filtration, and the reaction solution was concentrated into solid. The concentrate was dissolved in a mixed solvent of dichloromethane and methanol (50.0 mL, v:v=1:1), sodium methoxide was added to make pH=9-10, then reaction for 1.0 h at room temperature. When the reaction was complete by TLC detection, cation resin was added to neutralize the reaction solution, and after filtration, concentration and column chromatography, white solid IIIA (860.0 mg, 58.5% two-step yield) was obtained. 1H NMR (400 MHz, CD3OD) δ 5.09 (t, J=6.7 Hz, 1H), 4.44 (d, J=7.7 Hz, 1H), 3.80 (d, J=11.7 Hz, 1H), 3.76 (s, 3H), 3.64 (dd, J=11.7, 5.3 Hz, 1H), 3.36-3.31 (m, 2H), 3.27 (t, J=8.9 Hz, 1H), 3.20 (dd, J=7.3, 5.1 Hz, 1H), 3.10 (t, J=8.2 Hz, 1H), 2.88 (dt, J=8.5, 4.8 Hz, 1H), 2.52-2.43 (m, 2H), 2.31-2.22 (m, 1H), 2.10 (dd, J=12.7, 2.9 Hz, 1H), 1.66 (s, 3H), 1.62 (s, 3H), 1.29 (s, 3H), 1.14 (s, 3H), 1.11 (s, 3H), 1.07 (s, 3H), 1.05 (s, 3H), 0.74 (s, 3H); 13C NMR (150 MHz, CD3OD) δ 215.1, 166.5, 131.9, 126.0, 98.3, 82.5, 78.7, 77.4, 75.6, 71.7, 62.8, 61.3, 57.5, 57.2, 57.1, 55.8, 42.9, 41.9, 41.1, 40.8, 40.7, 39.6, 38.7, 35.1, 33.0, 28.1, 25.9, 24.9, 24.7, 23.5, 22.9, 20.3, 18.4, 17.8, 17.1, 16.2, 16.1. MALDI-HRMS calcd for C37H61NNaO8 [M+Na]+670.4289, found 670.4294.

Example 19 20(S)—O-β-D-glucopyranosyl dammarane-3-hydroxyl imino-24-ene-12-one (IIIB)

19.1 Synthesis of 12-β-hydroxyl-20(S)-hydroxyl dammarane-3-allyloxyimido-24-ene (III-4b)

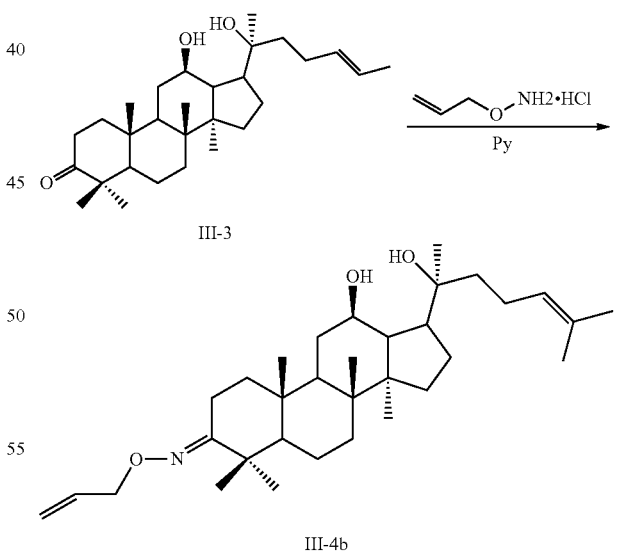

III-3 (5.0 g, 10.90 mmol) was dissolved in pyridine (120.0 mL), and O-allyl hydroxylamine hydrochloride (1.8 g, 16.35 mmol) was added. The reaction was allowed to take place under 80° C. for 4.0 h. The reaction solution was cooled to room temperature, water was added to stop the reaction, diluted with ethyl acetate, washed successively with 1 mol/L hydrochloric acid, saturated sodium bicarbonate and saturated sodium chloride, the organic layer was dried with anhydrous sodium sulfate, concentrated under reduced pressure, and directly used for the next reaction.

19.2 Synthesis of 20(S)-hydroxyl dammarane-3-allyloxyimido-24-ene-12-one (III-5b)

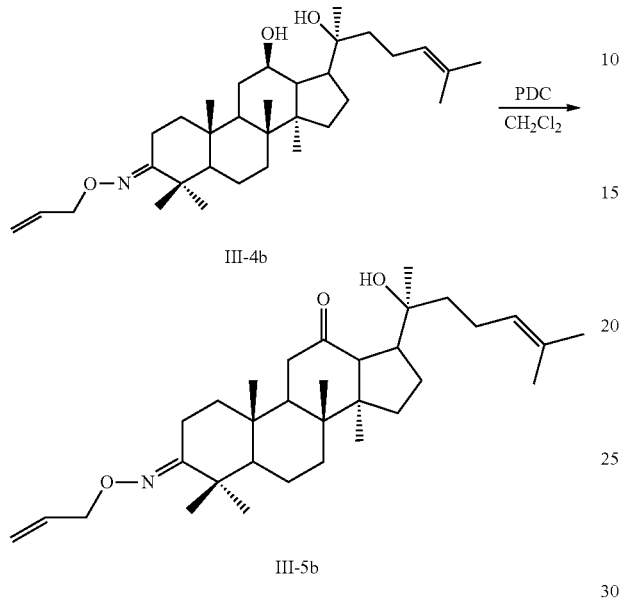

III-4b was dissolved in 120 mL of dry dichloromethane, PDC (6.2 g, 16.35 mmol) and acetic anhydride (3.1 mL, 32.70 mmol) were added. The reaction was performed under room temperature for about 5.0 h. The insoluble substance was removed by suction filtration. The filtrate was concentrated and separated by column chromatography, and light yellow foamed solid III-5b (3.6 g, 64.6% two-step yield) was obtained. 1H NMR (400 MHz, CDCl3) δ 5.99 (dd, J=17.4, 11.4 Hz, 1H), 5.26 (d, J=17.3 Hz, 1H), 5.17 (d, J=10.5 Hz, 1H), 5.09 (t, J=6.8 Hz, 1H), 4.52 (d, J=2.6 Hz, 2H), 3.24 (s, 1H), 2.97 (d, J=15.8 Hz, 1H), 2.86 (d, J=10.3 Hz, 1H), 2.43-2.36 (m, 1H), 1.69 (s, 3H), 1.62 (s, 3H), 1.20 (s, 3H), 1.16 (s, 3H), 1.12 (s, 3H), 1.06 (s, 3H), 1.01 (s, 3H), 0.79 (s, 3H); 13C NMR (150 MHz, CDCl3) δ 214.0, 165.3, 134.9, 131.7, 125.0, 117.0, 74.4, 73.2, 56.4, 56.0, 54.9, 53.1, 46.2, 40.3, 40.3, 39.3, 38.4, 37.9, 37.5, 33.7, 30.9, 27.6, 26.5, 25.9, 24.8, 23.2, 22.6, 19.2, 17.8, 17.8, 17.5, 15.9, 15.5. MALDI-HRMS calcd for C33H53NNaO3 [M+Na]+ 534.3918, found 534.3921.

19.3 Synthesis of 20(S)—O-β-D-glucopyranosyl dammarane-3-hydroxyl imino-24-ene-12-one (IIIB)

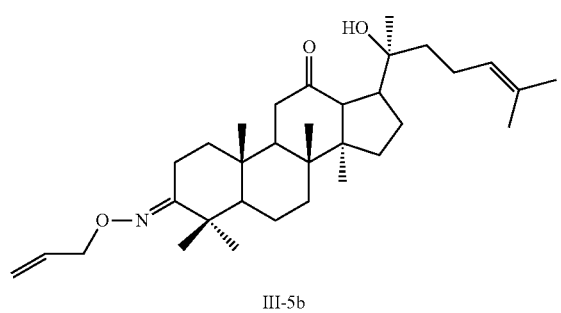

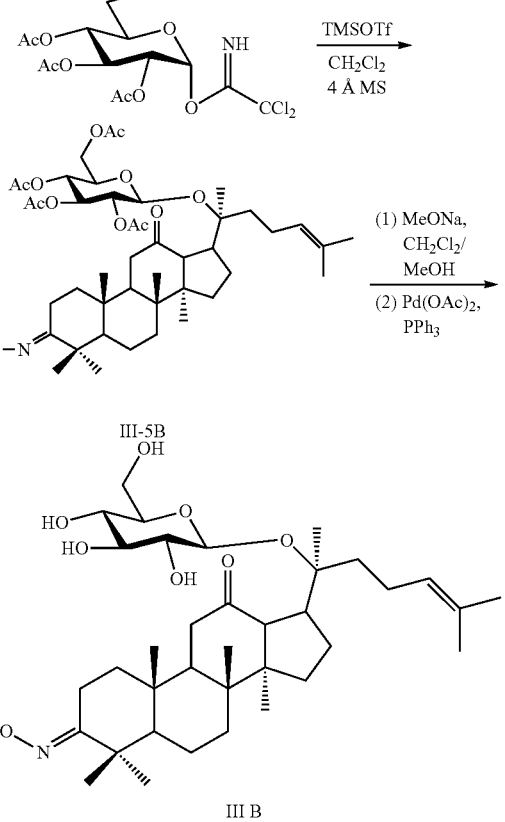

III-5b (3.6 g, 7.03 mmol) and 2,3,4,6-tetra-O-acetyl glucose trichloroimine ester (4.2 g, 8.44 mmol) were dissolved in dry CH$_2$Cl$_2$, appropriate amount of 4 Å molecular sieve was added, protected by argon, stirred for 30 min at room temperature, then the temperature of the reaction system was reduced to −40° C., and TMSOTf (127.0 μL, 0.70 mmol) was dripped for reaction at −40° C. After the reaction was detected through TLC until it was completed, Et$_3$N was added to stop the reaction, the reaction system restored to room temperature, the molecular sieve was removed by suction filtration, and the reaction solution was concentrated into solid. The concentrate was dissolved in a mixed solvent of dichloromethane and methanol (100.0 mL, v:v=1:1), sodium methoxide was added to make pH=9-10, and then reaction was allowed to take place for 1.0 h at room temperature. When the reaction was complete by TLC detection, cation resin was added to neutralize the reaction solution, after filtration and concentration, the concentrate was dissolved in the mixed solvent of ethanol and water (50.0 mL, v:v=4:1), triphenylphosphine (256.5 mg, 0.98 mmol), palladium acetate (73.2 mg, 0.33 mmol), triethylamine (4.1 mL, 29.34 mmol) and formic acid (1.1 mL, 29.34 mmol) were added, heated and refluxed for 1.5 h. The reaction solution was concentrated and purified by column chromatography, white solid IIIB (1.8 g, 40.4% three-step yield) was obtained. $^1$H NMR (400 MHz, CD$_3$OD) δ 5.09 (t, J=6.5 Hz, 1H), 4.44 (d, J=7.5 Hz, 1H), 3.80 (d, J=11.6 Hz, 1H), 3.65 (dd, J=11.8, 5.3 Hz, 1H), 3.36-3.31 (m, 2H), 3.28 (t, J=9.2 Hz, 1H), 3.22-3.19 (m, 1H), 3.10 (t, J=8.2 Hz, 1H), 2.96 (dt, J=14.6, 3.9 Hz, 1H), 2.53-2.44 (m, 2H), 2.33-2.24 (m, 1H), 2.11 (dd, J=12.2, 2.4 Hz, 1H), 1.66 (s, 3H), 1.62 (s, 3H), 1.30 (s, 3H), 1.14 (s, 3H), 1.11 (s, 3H), 1.07 (s, 3H), 1.06 (s, 3H), 0.74 (s, 3H); $^{13}$C NMR (150 MHz, CD$_3$OD) δ 215.2, 166.5, 131.9, 126, 98.3, 82.5, 78.7, 77.4, 75.6, 71.7, 62.8, 57.5, 57.2, 57.1, 55.9, 42.9, 41.9, 41.1, 40.8, 40.7, 39.6, 38.8, 35.1, 33.0, 28.1, 25.9, 24.9, 24.7, 23.4, 22.9, 20.3, 17.8, 17.7, 17.1, 16.12, 16.1. MALDI-HRMS calcd for C36H59NNaO8 [M+Na]+656.4133, found 656.4139.

Example 20 20(S)—O-β-D-glucopyranosyl dammarane-3-hydroxyl-2-cyano-2, 24-diene-12-one (IIIC)

20.1 Synthesis of 20(S)-hydroxyl dammarane-3-hydroxyl-2-cyano-2, 24-diene-12-one (III-9)

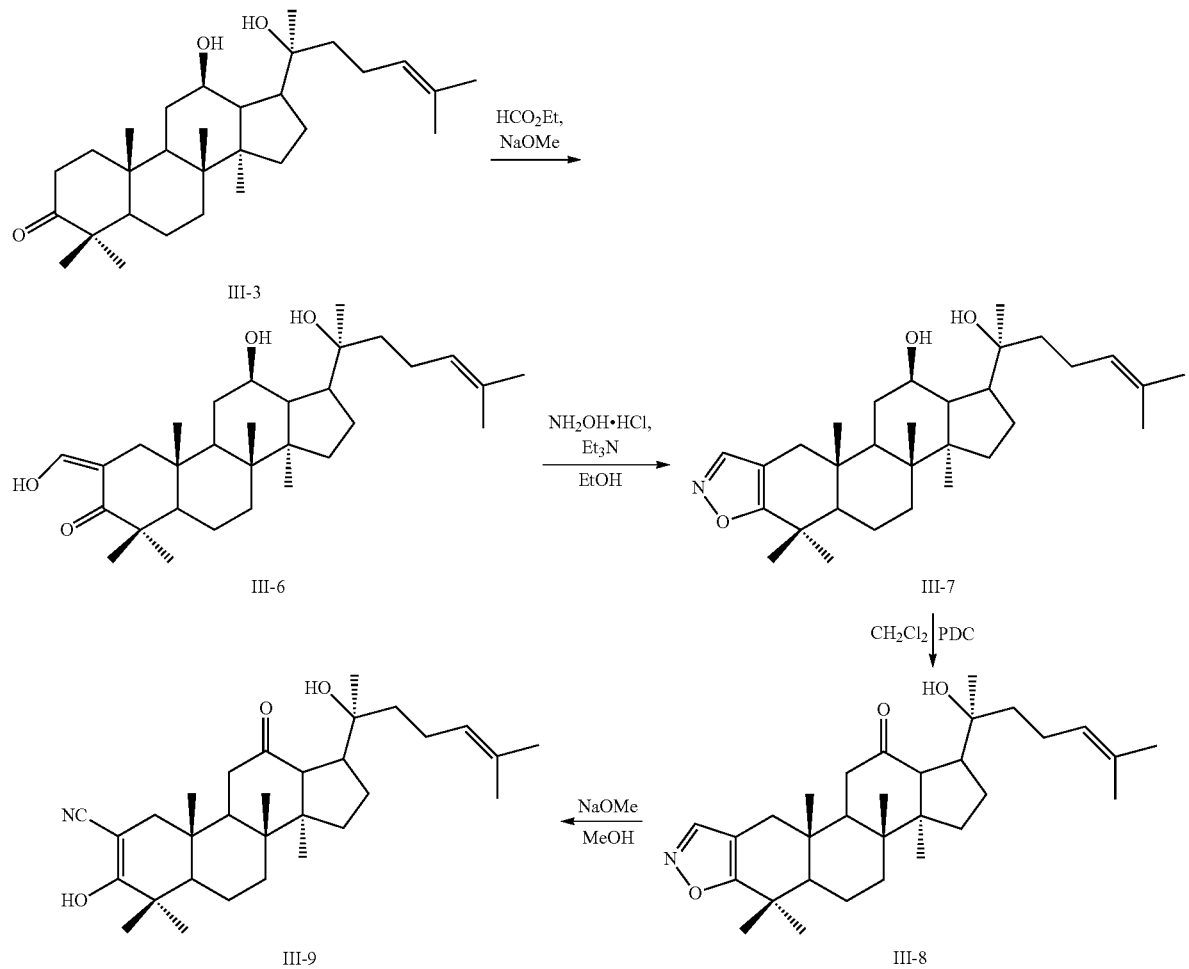

III-3 (10.0 g, 21.80 mmol) was dissolved in dried ethyl formate (150.0 mL), 30% sodium methoxide (30 mL) was added, and reacted at room temperature for 3.0 h. After reaction, diluted with ethyl acetate, washed successively with 1 mol/L hydrochloric acid, saturated sodium bicarbonate and saturated sodium chloride, the organic layer was dried with anhydrous sodium sulfate, and concentrated under reduced pressure. The concentrate was dissolved in the mixed solvent of ethanol (150.0 mL) and water (26.4 mL), hydroxylamine hydrochloride (3.0 g, 43.60 mmol) and triethylamine (3.0 mL, 21.80 mmol) were added. The reaction was allowed to take place at 55° C. for 10.0 h. After reaction, diluted with ethyl acetate, washed successively with 1 mol/L hydrochloric acid, saturated sodium bicarbonate and saturated sodium chloride, the organic layer was dried with anhydrous sodium sulfate, and concentrated under reduced pressure. The crude product was dissolved in 150.0 mL of dry dichloromethane, PDC (12.3 g, 32.70 mmol) and acetic anhydride (4.1 mL, 43.60 mmol) were added to react at room temperature for 6.0 h, the insoluble substance was removed by suction filtration, the filtrate was concentrated, the concentrate was dissolved in dry methanol (130.0 mL), and 30% sodium methoxide (5.4 mL) was added to react at 55° C. for 3.5 h. After reaction, diluted with ethyl acetate, washed successively with 1 mol/L hydrochloric acid, saturated sodium bicarbonate and saturated sodium chloride, the organic layer was dried with anhydrous sodium sulfate, concentrated under reduced pressure, separated by column chromatography, white solid III-9 (3.0 g, 28.6% four-step yield) was obtained. $^1$H NMR (600 MHz, (CD$_3$)$_2$SO) δ 9.78 (s, 1H), 5.06 (brs, 1H), 3.92 (s, 1H), 2.97 (d, J=9.3 Hz, 1H), 2.40 (t, J=13.1 Hz, 1H), 2.20 (brs, 1H), 1.63 (s, 3H), 1.57 (s, 3H), 1.17 (s, 3H), 1.10 (s, 3H), 1.01 (s, 3H), 0.90 (s, 3H), 0.87 (s, 3H), 0.66 (s, 3H); $^{13}$C NMR (150 MHz, (CD$_3$)$_2$SO) δ 210.3, 171.5, 130.1, 125.1, 119.9, 77.9, 72.3, 55.4, 55.4, 51.8, 51.7, 42.3, 41.5, 40.5, 38.1, 35.9, 32.8, 31.4, 26.9, 25.5, 25.3, 23.3, 22.6, 19.0, 17.5, 16.5, 15.2, 14.8. MALDI-HRMS calcd for C31H47NNaO3 [M+Na]+ 504.3448, found 504.3452.

20.2 20(S)—O-β-D-glucopyranosyl dammarane-3-hydroxyl-2-cyano-2,24-diene-12-one (IIIC)

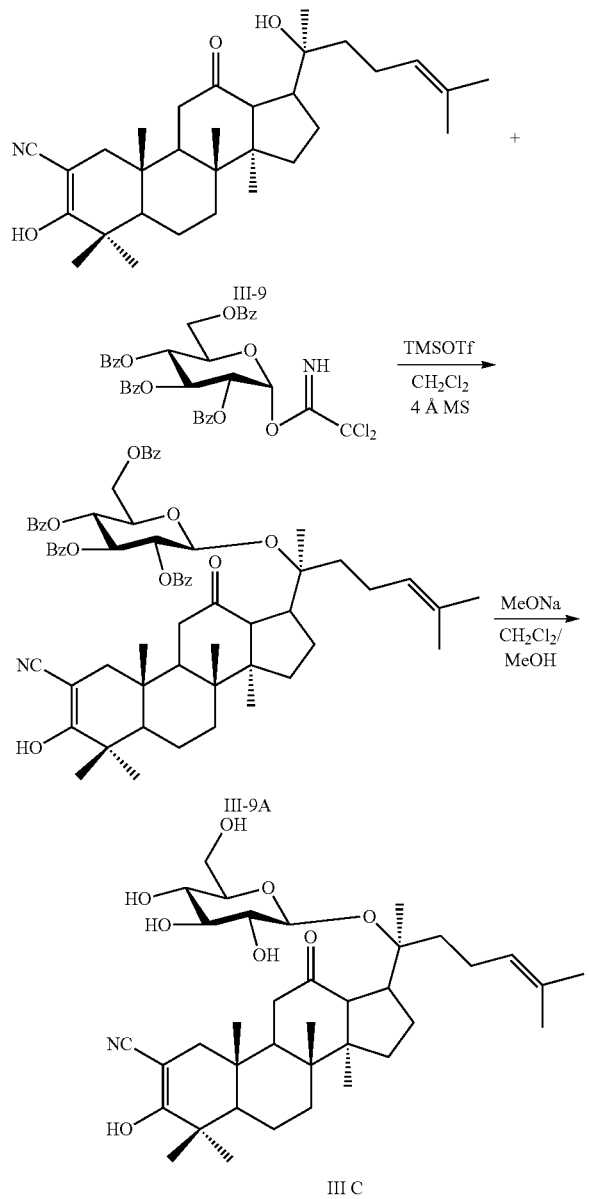

III-9 (2.0 g, 4.15 mmol) and 2,3,4,6-tetra-O-benzoyl glucose trichloroimine ester (3.7 g, 4.98 mmol) were dissolved in dried CH2Cl2 (90.0 mL), and appropriate amount of 4 Å molecular sieve was added, protected by argon. It was stirred for 30 min at room temperature, then the temperature of the reaction system was reduced to 0° C., and TMSOTf (75.0 μL, 0.42 mmol) was dripped for reaction at 0° C. After the reaction was detected through TLC until it was completed, Et3N was added to stop the reaction, the reaction system was restored to room temperature, the molecular sieve was removed by suction filtration, and the reaction solution was concentrated into solid. The concentrate was dissolved in a mixed solvent of dichloromethane and methanol (50.0 mL, v:v=1:1), sodium methoxide was added to make pH=9-10, and then reaction was allowed to take place for 4.0 h at room temperature. When the reaction was complete by TLC detection, cation resin was added to neutralize the reaction solution, after filtration, concentration and column chromatography, white solid IIIC (1.6 g, 59.9% two-step yield) was obtained. 1H NMR (400 MHz, CD3OD) δ 5.09 (t, J=6.5 Hz, 1H), 4.44 (d, J=7.7 Hz, 1H), 3.80 (dd, J=11.8, 1.9 Hz, 1H), 3.64 (dd, J=11.9, 5.3 Hz, 1H), 3.38-3.34 (m, 2H), 3.27 (d, J=8.8 Hz, 1H), 3.22-3.17 (m, 1H), 3.10 (t, J=8.2 Hz, 1H), 2.56-2.48 (m, 2H), 1.66 (s, 3H), 1.62 (s, 3H), 1.29 (s, 3H), 1.16 (s, 3H), 1.12 (s, 3H), 1.09 (s, 4H), 1.02 (s, 3H), 0.76 (s, 3H); 13C NMR (150 MHz, CD3OD) δ 214.7, 173.6, 131.9, 126.0, 120.6, 98.3, 82.5, 79.4, 78.7, 77.4, 75.6, 71.7, 62.8, 57.6, 57.1, 54.4, 53.9, 42.9, 42.4, 41.6, 40.7, 40.6, 39.7, 37.7, 34.5, 33.0, 27.9, 25.9, 24.9, 24.7, 22.9, 20.6, 19.8, 17.8, 17.0, 16.0, 15.7. MALDI-HRMS calcd for C37H57NNaO8 [M+Na]+666.3976, found 666.3973.

Example 21 20(S)—O-β-D-glucopyranosyl dammarane-3,12-hydroxyl imino-24-ene-12-one (IVA)

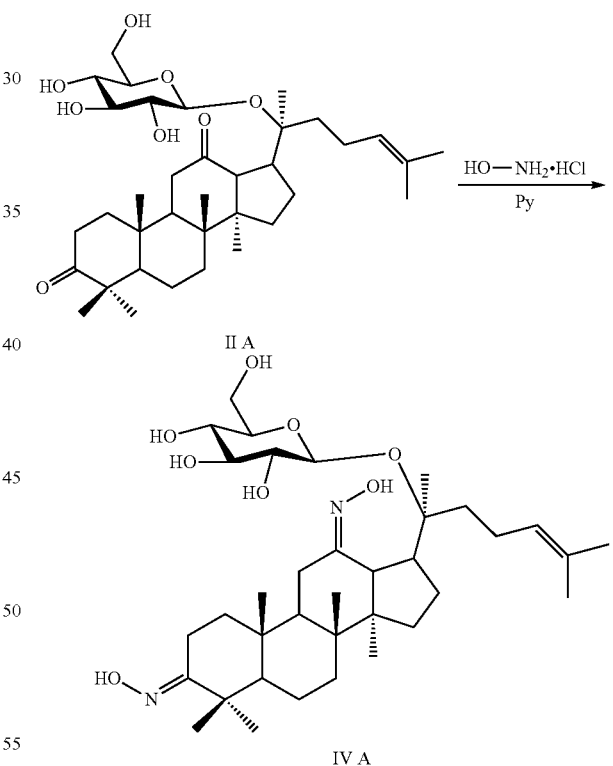

IIA (1.25 g, 2.02 mmol) was dissolved in pyridine (60.0 mL), hydroxylamine hydrochloride (421.1 mg, 6.06 mmol) was added. The reaction was allowed to take place at 80° C. for 4.0 h. The reaction solution was cooled to room temperature, water was added to stop the reaction, diluted with ethyl acetate, washed successively with 1 mol/L hydrochloric acid, saturated sodium bicarbonate and saturated sodium chloride, the organic layer was dried with anhydrous sodium sulfate, concentrated under reduced pressure, purified by column chromatography, and white solid IVA (913.0 mg, 69.7%) was obtained. 1H NMR (400 MHz, CD3OD) δ 5.09 (t, J=6.8 Hz, 1H), 4.46 (d, J=7.6 Hz, 1H), 3.80 (d, J=11.4 Hz, 1H), 3.65 (dd, J=11.5, 5.1 Hz, 1H), 3.37-3.33 (m, 2H), 3.30-3.28 (m, 1H), 3.20 (dd, J=14.6, 7.8 Hz, 1H), 3.11 (t, J=8.0 Hz, 1H), 2.94-2.88 (m, 1H), 2.85 (d, J=9.6 Hz, 1H), 2.59 (dd, J=11.0, 6.9 Hz, 1H), 2.38-2.30 (m, 1H), 1.66 (s, 3H), 1.60 (s, 3H), 1.22 (s, 3H), 1.18 (s, 3H), 1.13 (s, 3H), 1.06 (s, 3H), 1.03 (s, 3H), 0.77 (s, 3H); 13C NMR (150 MHz, CD3OD) δ 166.9, 161.8, 131.8, 126.2, 98.4, 83.4, 78.6, 77.3, 75.4, 71.8, 62.9, 57.0, 55.5, 53.2, 43.4, 41.9, 41.1, 40.5, 39.9, 38.8, 35.6, 32.5, 28.2, 25.9, 24.4, 23.4, 22.7, 20.2, 17.8, 17.3, 16.3, 15.8. MALDI-HRMS calcd for C36H60N2NaO8 [M+Na]+671.4242, found 671.4246.

Example 22 the Research of the Effect of Compounds on Asthma Induced by Ovalbumin in Balb/c Mice In this experiment, the above-mentioned ginsenoside derivatives (hereinafter referred to as GR derivatives) and ginsenoside CK were selected.

Drug preparation: the corresponding amount of sample was ground in a mortar, and then 0.5% CMCNa was used to prepare the corresponding volume by the method of equivalent multiplication.

Positive Control:

This series involve oral administration. Dexamethasone acetate tablets (manufacturer: Shanghai Xinyi Pharmaceutical Co., Ltd., batch number, specification: 015150901, 0.75 mg) were selected as positive drugs.

Ginsenoside CK (manufacturer: Shanghai Standard Biotech Co. Ltd, batch number, specification: 3690/20548, 5000.0 mg, purity: 92%)

Reagents

OVA (ovalbumin): batch No. SLBF4846V, specification 500 g/bottle, Sigma-Aldrich (USA).

Mouse IgE ELISA Kit: Cat EK2752, Lot 227570132, valid until July 2018, Multi Sciences (Lianke) Biotech.

Mouse IgE ELISA Kit: Cat EK2752, Lot 227570341, valid until Sep. 2018 9, Multi Sciences (Lianke) Biotech.

Mouse IgE ELISA Kit: Cat EK2752, Lot 227570842, valid until Feb. 2019 2, Multi Sciences (Lianke) Biotech.

Preparation of aluminum hydroxide adjuvant: under strong agitation, 100 mL of 5% sodium hydroxide solution was added into 250 mL of 5% aluminum sulfate solution. The precipitates were centrifuged and washed twice with normal saline, and then suspended into normal saline to make it reach 250 mL.

Equipment

Nebulizer: model: 403C household air compression nebulizer, manufacturer: Yuwell medical.

Laboratory Animals

Animals were purchased from Shanghai Sippr-BK laboratory animal Co., Ltd. License No.: SCXK (Shanghai) 2013-0016.

Experimental Method

Groups and Dosages

The 1st time: Balb/c mice, female, weight 18-20 g, were divided into blank group, model group, dexamethasone 0.6 mg/kg group, CK group, GR derivative group, 5 in each group, oral administration.

The 2nd time: Balb/c mice, female, weight 18-20 g, were divided into blank group, model group, dexamethasone 0.6 mg/kg group, CK group, GR derivative group, 5 in each group, oral administration.

Experimental Method:

In addition to the blank group, the mice were sensitized by intraperitoneal injection of OVA (20 μg OVA/mice) on day 0 and day 14. Stimulated by atomization administration of OVA on day 21-25. 24 hours after the last stimulation, blood was collected from the canthus of mice, serum was taken, and the level of IgE in serum was determined by ELISA kit.

Data Analysis

The data were represented by mean and standard deviation ($\bar{x}$±s). SPSS16.0 software was used for one way ANOVA to compare the differences of each group. If $p<0.05$, it was considered to have statistical significance.

6 Results

TABLE 1-1

Effect of samples on the concentration of IgE in serum of mouse asthma model induced by OVA

| Groups | Concentration (ng/mL) |
|---|---|
| blank group | 176.70 ± 36.97** |
| model group | 2244.05 ± 429.07 |
| Dexamethasone acetate tablets 0.6 mg/kg | 1131.05 ± 211.85** |
| CK-20 mg/kg | 1701.85 ± 284.66* |
| IC 20 mg/kg | 975.82 ± 260.32** |
| ID 20 mg/kg | 1336.96 ± 211.85** |
| IB 20 mg/kg | 1337.11 ± 216.28** |
| IVA 20 mg/kg | 1358.27 ± 248.70** |
| IH 20 mg/kg | 1191.08 ± 107.59** |
| IJ 20 mg/kg | 1250.07 ± 144.38** |
| IK 20 mg/kg | 1020.78 ± 136.94** |
| IL 20 mg/kg | 996.36 ± 102.45** |

Compared to model group:
*p < 0.05,
**p < 0.01

TABLE 1-2

Effect of samples on the concentration of IgE in serum of mouse asthma model induced by OVA

| Groups | Concentration (ng/mL) |
|---|---|
| blank group | 80.59 ± 10.16** |
| model group | 2322.52 ± 296.04 |
| Dexamethasone acetate tablets 0.6 mg/kg | 1367.07 ± 103.80** |
| CK 15 mg/kg | 1921.25 ± 160.12* |
| CK 30 mg/kg | 1676.69 ± 159.13* |
| CK 60 mg/kg | 1501.85 ± 110.68* |
| IB 15 mg/kg | 2023.33 ± 203.47 |
| IB 30 mg/kg | 1909.19 ± 121.73 |
| IB 60 mg/kg | 1769.13 ± 164.34* |
| IC 15 mg/kg | 1908.70 ± 221.74 |
| IC 30 mg/kg | 1738.93 ± 124.22 |
| IC 60 mg/kg | 1575.92 ± 148.33* |
| ID 15 mg/kg | 1571.67 ± 134.04* |
| ID 30 mg/kg | 1427.83 ± 164.28** |
| ID 60 mg/kg | 1264.95 ± 127.60** |
| IVA 15 mg/kg | 2026.13 ± 273.15 |
| IVA 30 mg/kg | 1927.60 ± 151.61 |
| IVA 60 mg/kg | 1723.86 ± 167.59* |
| IH 15 mg/kg | 1682.40 ± 182.76* |
| IH 30 mg/kg | 1311.37 ± 165.93* |
| IH 60 mg/kg | 1150.59 ± 129.55** |
| IJ 15 mg/kg | 2068.41 ± 153.29 |
| IJ 30 mg/kg | 1824.85 ± 155.74 |
| IJ 60 mg/kg | 1622.18 ± 130.38* |
| IK 15 mg/kg | 1720.54 ± 165.49* |
| IK 30 mg/kg | 1406.28 ± 171.05** |
| IK 60 mg/kg | 1217.43 ± 162.75** |
| IL 15 mg/kg | 1548.67 ± 190.16* |
| IL 30 mg/kg | 1311.37 ± 154.37** |
| IL 60 mg/kg | 1080.12 ± 131.23** |

Compared to model group:
*p < 0.05,
**p < 0.01

Conclusion: in the model of mouse asthma induced by OVA, Samples ID, IH, IK and IL can significantly reduce the content of IgE in mice serum, and 0.6 mg/kg dexamethasone can also significantly reduce the content of IgE in mice serum. ID, IH, IK and IL have obvious therapeutic effect on bronchial asthma induced by OVA.

Example 23 Determination of Inflammatory Cells in Bronchoalveolar Lavage Fluid of Mice 144 6-week-old BALB/C mice (18-20 g) were divided into 24 groups: control group, placebo group, dexamethasone group (3 mg/kg) and the drug groups. There were 6 in each group. The control group was given normal saline without any treatment. The other groups were sensitized by intraperitoneal injection of OVA 20 μg and aluminum hydroxide 200 μL PBC (2 mg, prepared into emulsion). Each animal was given sensitization stimulation by inhalation of 3% OVA 30 minutes on day 0 and day 14. On day 21, 22 and 23, the therapeutic agent (i.e. 3 mg/kg dexamethasone in the positive control group and oral administration in the drug group) was given orally. From day 17 to 23, PBS was given to the control group and placebo group respectively, PBS (without OVA) was given to the control group. On day 0 and day 14, the normal saline was nebulized for 30 minutes to remove the aluminum hydroxide on day 21, 22 and 23 See in Table 2.

Animal pulmonary function analysis system: model: AniRes2005. Manufacturer: Beijing belanbo Technology Co., Ltd.

Passive smoking animal exposure system: model: PABS200. Manufacturer: Beijing belanbo Technology Co., Ltd.

Animal Wistar rats, male, weight 160 g, clean grade, purchased from Shanghai SLAC Laboratory Animal Co., Ltd, production license No.: SCXK (Shanghai) 2013-0016.

Experimental Method:

(1) Smoke generation and inhalation: In addition to the blank group, the cigarettes were put into the smoke generator (20 cigarettes/time), the rats were placed in the nebulization inhalation box, the size of the nebulization box is 60 cm×60 cm×80 cm, after the cigarettes were lighted, the smoke was injected into the poisoning box through the automatic suction function of the syringe, and all the cigarettes were burned out within five minutes. Twice a day in the morning and evening, 30 minutes each time, more than 4 hours apart, 180 consecutive days.

(2) Budesonide administration:

Budesonide formulation was diluted with normal saline and then put into an nebulizing cup for administration. The concentration of nebulizing solution in 0.25 mg/mL group was 0.25 mg/mL, 4 mL each time. Each nebulization administration was last for 30 minutes.

TABLE 2

The results of determination of inflammatory cells in bronchoalveolar lavage fluid of mice

| | | Dosage | Total | Acidic | Neutral | lymphocyte |
|---|---|---|---|---|---|---|
| Model group | | | 72.36 ± 33.42 | 38.08 ± 15.16 | 14.08 ± 6.15 | 12.71 ± 7.12 |
| Sample groups | IB | 2 mg/kg | 46.76 ± 25.18* | 31.19 ± 8.46 | 12.11 ± 7.22 | 10.07 ± 6.12 |
| | | 20 mg/kg | 25.18 ± 13.12** | 9.35 ± 4.16*** | | 7.53 ± 4.95* |
| | | 200 mg/kg | 12.53 ± 6.23** | 5.14 ± 3.08*** | 3.49 ± 2.37*** | 3.75 ± 2.18*** |
| | IA | 2 mg/kg | 40.75 ± 26.14* | 29.23 ± 10.29 | 10.40 ± 6.48 | 11.81 ± 5.97 |
| | | 20 mg/kg | 26.93 ± 15.01** | 11.46 ± 4.12*** | 6.38 ± 3.45** | 8.84 ± 5.63 |
| | | 200. mg/kg | 10.85 ± 4.62*** | 7.37 ± 5.5.13*** | 2.08 ± 2.01*** | 4.27 ± 3.16*** |
| | IA-1 | 2 mg/kg | 43.42 ± 26.14* | 26.55 ± 13.23* | 10.21 ± 6.07 | 13.22 ± 8.27 |
| | | 20 mg/kg | 28.11 ± 14.91** | 13.26 ± 3.92*** | 3.95 ± 2.41*** | 4.76 ± 3.18*** |
| | | 200 mg/kg | 11.48 ± 4.39*** | 5.22 ± 3.31*** | 3.75 ± 2.46*** | 3.82 ± 2.66*** |
| | IVA | 2 mg/kg | 51.47 ± 3172 | 29.09 ± 4.83 | 9.15 ± 5.68 | 15.35 ± 9.23 |
| | | 20 mg/kg | 32.46 ± 17.21** | 15.83 ± 2.88** | 7.38 ± 3.09** | 5.24 ± 3.34** |
| | | 200 mg/kg | 14.69 ± 5.77*** | 4.45 ± 2.14*** | 6.17 ± 4.09** | 4.19 ± 3.48** |
| | IC | 2 mg/kg | 50.77 ± 32.49 | 31.51 ± 16.14 | 13.29 ± 7.12 | 9.30 ± 6.85 |
| | | 20 mg/kg | 32.95 ± 21.07** | 18.44 ± 7.78** | 8.16 ± 5.03** | 6.49 ± 5.28** |
| | | 200 mg/kg | 18.25 ± 9.48*** | 8.72 ± 3.31*** | 5.17 ± 3.19** | 3.77 ± 2.81*** |
| | ID | 2 mg/kg | 46.39 ± 22.74 | 34.15 ± 18.88 | 13.18 ± 7.76 | 14.38 ± 8.71 |
| | | 20 mg/kg | 29.46 ± 13.56** | 15.17 ± 8.34** | 6.26 ± 4.73** | 8.92 ± 6.89 |
| | | 200 mg/kg | 13.81 ± 6.76*** | 6.79 ± 3.87*** | 4.39 ± 3.13*** | 4.16 ± 317*** |
| | CK | 2 mg/kg | 52.29/34.92 | 32.47 ± 20.33 | 15.24 ± 7.94 | 16.81 ± 9.88 |
| | | 20 mg/kg | 24.87 ± 20.58** | 16.39 ± 9.67** | 8.78 ± 5.33** | 10.15 ± 7.34 |
| | | 200 mg/kg | 22.38 ± 12.69** | 13.12 ± 7.38** | 4.32 ± 3.16*** | 7.42 ± 4.53 |
| | DEX | 3 mg/kg | 36.12 ± 14.89** | 7.49 ± 5.25*** | 9.64 ± 5.16** | 8.46 ± 5.73 |

The results showed that: the inflammatory cells in bronchoalveolar lavage fluid of the mice in asthma model group showed a large number of inflammatory cells converged, while the inflammatory cells in the bronchoalveolar lavage fluid of the mice in GR derivative group showed that the number of inflammatory cells in GR derivative group was significantly lower than that in model group.

Example 24 Study on Effects of GR Derivatives on COPD Induced by Smoke Exposure in Rats Budesonide suspension for inhalation (batch No. 318205, manufacturer: AstraZeneca Pty Ltd.)

Huangguoshu cigarette, tar content 11 mg/cigarette, Guizhou Zhongyan Industry Co., Ltd.

Nebulizer: model: 403C household air compression nebulizer, manufacturer: Yuwell medical.

(3) CK and GR derivative administration:

It was divided into blank group, model group, budesonide, CK and GR derivatives: IB, IC, ID, IVA, IH, IJ, IK, IL oral administration groups, the dosage gradient of CK and GR derivatives was 20 mg/kg, 40 mg/kg, 80 mg/kg. 5 animals in each group, and the drugs were administered continuously for 180 days after grouping. The lung function was measured after the experiment. The rats were anesthetized with pentobarbital sodium and then intubated. The related indexes of forced pulmonary ventilation (FVC) in each animal. were measured by AniRes2005 pulmonary function tester. The related indexes of lung function of rats were analyzed by software.

Experimental Results:

TABLE 3

Effects of tested substance on FEV0.2/FVC % (forced expiratory index within 200 ms) of COPD rats

| Groups | FEV2/FVC % |
| --- | --- |
| Blank | 72.23 ± 15.92* |
| Model | 55.45 ± 9.11 |
| Budesonide | 79.47 ± 12.39** |
| CK 20 mg/kg | 61.29 ± 11.76 |
| CK 40 mg/kg | 70.89 ± 10.56** |
| CK 80 mg/kg | 80.24 ± 13.73** |
| IB 20 mg/kg | 65.14 ± 12.78 |
| IB 40 mg/kg | 73.59 ± 10.81* |
| IB 80 mg/kg | 82.16 ± 9.01** |
| IC 20 mg/kg | 65.45 ± 14.17 |
| IC 40 mg/kg | 76.64 ± 7.98** |
| IC 80 mg/kg | 83.15 ± 8.42** |
| ID 20 mg/kg | 66.28 ± 13.54 |
| ID 40 mg/kg | 75.23 ± 10.71* |
| ID 80 mg/kg | 86.34 ± 8.60** |
| IVA 20 mg/kg | 66.25 ± 11.49 |
| IVA 40 mg/kg | 75.98 ± 9.26* |
| IVA 80 mg/kg | 88.33 ± 12.49** |
| IH 20 mg/kg | 63.27 ± 14.65 |
| IH 40 mg/kg | 73.59 ± 12.14* |
| IH 80 mg/kg | 85.51 ± 15.27** |
| IJ 20 mg/kg | 65.78 ± 12.35 |
| IJ 40 mg/kg | 77.57 ± 9.69* |
| IJ 80 mg/kg | 84.36 ± 7.10** |
| IK 20 mg/kg | 67.67 ± 11.39 |
| IK 40 mg/kg | 78.59 ± 6.12* |
| IK 80 mg/kg | 85.56 ± 10.07** |
| IL 20 mg/kg | 71.15 ± 10.34* |
| IL 40 mg/kg | 80.25 ± 8.79** |
| IL 80 mg/kg | 89.62 ± 5.14** |

Compared to model group:
*p < 0.05,
**p < 0.01

Conclusion: in the model of COPD rats induced by smoke exposure, budesonide was inhaled and the other compounds were orally administered. The high dose group of CK, IB, IC, ID, IVA, IH, IJ, IK and IL was superior to budesonide. Therefore, GR derivatives have a good effect on COPD.

Example 25 Blood Routine

33 ICR mice were randomly divided into 11 groups, i.e. normal saline group, 1.8 mg/kg dexamethasone acetate group (Dex), CK, IB, IC, ID, IVA, IH, IJ, IK and IL were all given 225 mg/kg. Mice were intragastric administration for 6 consecutive days, and sufficient blood samples were taken for blood routine test 1 hour after the last dose.

TABLE 4

Blood test data of GR series compounds

| | WBC*$10^2$/mm$^3$ | Ne % | Ly % | Eo % | Mo % | Ba % |
| --- | --- | --- | --- | --- | --- | --- |
| normal saline group | 6.13 ± 1.52 | 28.21 ± 3.64 | 62.34 ± 20.72 | 0.83 ± 0.79 | 7.55 ± 3.62 | 0.07 ± 0.03 |
| dexamethasone acetate group | 1.26 ± 0.49** | 45.17 ± 16.22** | 42.59 ± 28.17** | 0.09 ± 0.02 | 12.08 ± 6.28** | 0.04 ± 0.03 |
| CK | 4.96 ± 2.14 | 31.39 ± 2.72 | 62.54 ± 30.29 | 0.75 ± 0.71 | 6.01 ± 8.91 | 0.01 ± 0.02 |
| IB | 5.27 ± 0.98 | 37.81 ± 10.97 | 51.35 ± 16.33 | 0.05 ± 0.06 | 10.75 ± 1.93 | 0.05 ± 0.04 |
| IC | 6.39 ± 2.27 | 35.01 ± 10.73 | 56.37 ± 29.01 | 0.10 ± 0.33 | 8.52 ± 2.30 | 0.01 ± 0.11 |
| ID | 4.92 ± 1.45 | 37.89 ± 12.34 | 53.03 ± 15.16 | 0.10 ± 0.03 | 7.95 ± 2.88 | 0.08 ± 0.02 |
| IVA | 6.48 ± 1.34 | 22.80 ± 13.42 | 70.15 ± 19.03 | 0.07 ± 0.02 | 7.87 ± 1.02 | 0.08 ± 0.04 |
| IH | 4.92 ± 2.07 | 33.45 ± 9.64 | 60.41 ± 12.90 | 0.11 ± 0.23 | 8.74 ± 3.07 | 0.09 ± 0.10 |
| IJ | 4.76 ± 1.12 | 34.17 ± 8.37 | 61.68 ± 13.75 | 0.12 ± 0.05 | 9.55 ± 2.12 | 0.07 ± 0.02 |
| IK | 6.37 ± 0.73 | 30.89 ± 12.03 | 59.04 ± 12.36 | 0.08 ± 0.04 | 11.27 ± 1.82 | 0.02 ± 0.02 |
| IL | 4.25 ± 1.35 | 26.28 ± 10.92 | 62.12 ± 2.18 | 0.15 ± 0.13 | 10.56 ± 2.44 | 0.03 ± 0.01 |

Note:
compared to blank group,
*P < 0.05,
**P < 0.01

The hematological data showed that compared to the blank control group, the lymphocyte percentage of 1.8 mg/kg dexamethasone group decreased significantly, the neutrophil percentage increased significantly, the leukocyte count decreased significantly, the monocyte percentage increased significantly; while no hematological related changes were caused by CK and GR derivatives.

Example 26 Blood Glucose of Caudal Vein

33 ICR mice were randomly divided into 11 groups, i.e. normal saline group, 1.8 mg/kg dexamethasone acetate group (Dex), CK, IB, IC, ID, IVA, IH, IJ, IK and IL were respectively given 225 mg/kg. The mice were intragastric administration for 6 consecutive days, fasting was started at about 8:00 in the morning on the sixth day, and blood glucose in caudal vein was measured at about 4:00 in the next day.

TABLE 5

| Blood glucose data of GR series compounds | |
|---|---|
| Group | Blood glucose (mmol/L) |
| Blank group | 3.05 ± 0.11 |
| Dex | 5.78 ± 0.36** |
| CK | 3.18 ± 0.28 |
| IB | 3.10 ± 0.19 |
| IC | 3.25 ± 0.26 |
| ID | 2.79 ± 0.56 |
| IVA | 3.02 ± 0.23 |
| IH | 2.98 ± 0.37 |
| IJ | 3.11 ± 0.43 |
| IK | 3.09 ± 0.28 |
| IL | 3.03 ± 0.21 |

Note:
compared to blank group,
* P < 0.05,
**P < 0.01

Blood glucose data showed that compared with the blank control group, dexamethasone could increase blood glucose in mice, while no blood glucose related changes were caused by CK and GR derivatives.

The invention claimed is:

1. A panaxadiol glycoside derivative represented by the structure of general formula (I) or a pharmaceutically acceptable salt thereof,

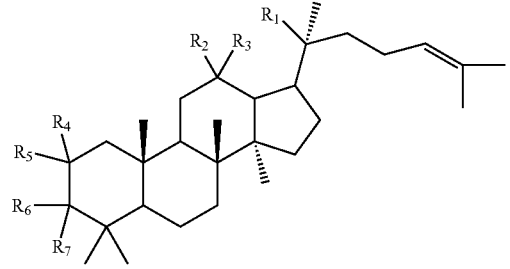

(I)

wherein, $R_1$ is selected from rhamnopyranosyl, fucosyl, arabinosyl, xylosyl, ribosyl, quinovosyl, galactosyl, aminoglucosyl, 6-deoxy-6-aminoglucosyl, lactosyl, cellobiosyl or

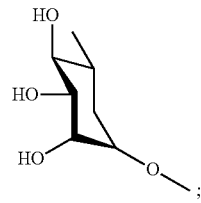

$R_2$ together with $R_3$ represents =O or =N—$OR_8$;
or $R_2$ is hydrogen and $R_3$ is hydroxyl;
$R_4$ and $R_6$ combine to form a bond, and $R_5$ and $R_7$ are independently selected from hydrogen, $C_{1-6}$ alkoxy, hydroxyl, cyano group, $C_{1-6}$ ester group, and glycosyl;
or $R_6$ together with $R_7$ represents =O or =N—OH, and $R_5$ and $R_4$ are independently selected from hydrogen, $C_{1-6}$ alkoxy, hydroxyl, and cyano group;
$R_8$ is selected from hydrogen or methyl; and
wherein the glycosyl is independently selected from deoxy glycosyl or a five-carbon glycosyl.

2. The panaxadiol glycoside derivative or a pharmaceutically acceptable salt thereof according to claim 1, wherein, $R_2$ together with $R_3$ represents =N—OH.

3. The panaxadiol glycoside derivative or a pharmaceutically acceptable salt thereof according to claim 1, wherein, $R_4$ and $R_6$ combine to form a bond.

4. The panaxadiol glycoside derivative or a pharmaceutically acceptable salt thereof according to claim 3, wherein, $R_5$ is selected from glycosyl.

5. The panaxadiol glycoside derivative or a pharmaceutically acceptable salt thereof according to claim 1, wherein, $R_6$ together with $R_7$ represents =N—$OR_8$.

6. The panaxadiol glycoside derivative or a pharmaceutically acceptable salt thereof according to claim 1, wherein the structure of the panaxadiol glycoside derivative is as follows:

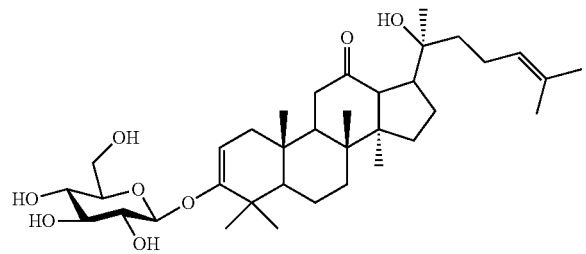

(IIA-1)

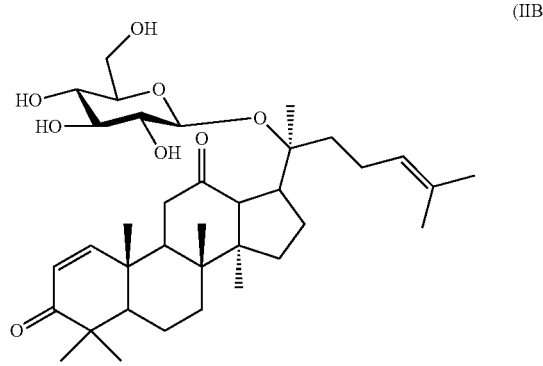

(IIB)

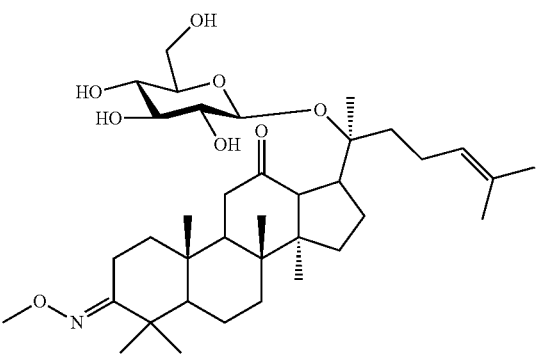

(IIIA)

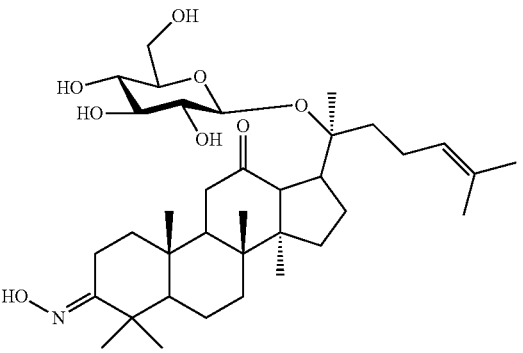

(IIIB)

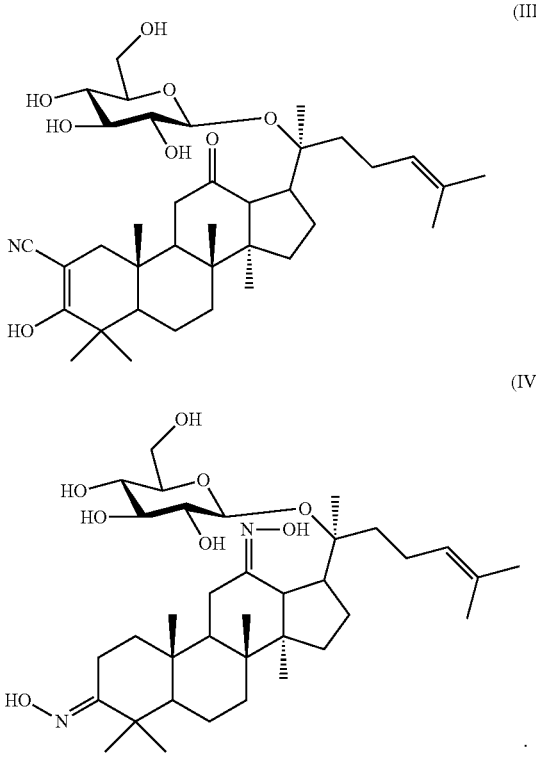

7. A pharmaceutical composition containing the panaxadiol glycoside derivative or a pharmaceutically acceptable salt thereof according to claim 1 and a pharmaceutically acceptable excipient.

8. A method of treating a patient suffering from at least one condition selected from the group consisting of asthma and COPD comprising administering to the patient a panaxadiol glycoside derivative or a pharmaceutically acceptable salt thereof according to claim 1.

9. The method according to claim 8, wherein the panaxadiol glycoside derivative or a pharmaceutically acceptable salt is the panaxadiol glycoside derivative or a pharmaceutically acceptable salt of claim 2.

10. The method according to claim 8, wherein the panaxadiol glycoside derivative or a pharmaceutically acceptable salt is the panaxadiol glycoside derivative or a pharmaceutically acceptable salt of claim 3.

11. The method according to claim 8, wherein the panaxadiol glycoside derivative or a pharmaceutically acceptable salt is the panaxadiol glycoside derivative or a pharmaceutically acceptable salt of claim 4.

12. The method according to claim 8, wherein the panaxadiol glycoside derivative or a pharmaceutically acceptable salt is the panaxadiol glycoside derivative or a pharmaceutically acceptable salt of claim 5.

13. The method according to claim 8, wherein the panaxadiol glycoside derivative or a pharmaceutically acceptable salt is the panaxadiol glycoside derivative or a pharmaceutically acceptable salt of claim 6.

* * * * *